United States Patent
Bui et al.

(10) Patent No.: US 6,689,091 B2
(45) Date of Patent: *Feb. 10, 2004

(54) MEDICAL APPARATUS WITH REMOTE CONTROL

(76) Inventors: Tuan Bui, 14436 Greenfield Ct., Green Oaks, IL (US) 60048; Larry Wilson, 14111 Segundo Ct., Poway, CA (US) 92064

( * ) Notice: Subject to any disclaimer, the term of this patent is extended or adjusted under 35 U.S.C. 154(b) by 38 days.

This patent is subject to a terminal disclaimer.

(21) Appl. No.: 10/039,751

(22) Filed: Jan. 3, 2002

(65) Prior Publication Data

US 2002/0143290 A1 Oct. 3, 2002

Related U.S. Application Data

(63) Continuation-in-part of application No. 09/272,502, filed on Mar. 19, 1999, now abandoned, which is a continuation of application No. 08/951,976, filed on Oct. 16, 1997, now Pat. No. 5,885,245, which is a continuation-in-part of application No. 08/691,687, filed on Aug. 2, 1996, now abandoned.

(51) Int. Cl.$^7$ .............................................. A61M 31/00
(52) U.S. Cl. ........................................ 604/67; 604/131
(58) Field of Search ............................. 604/31, 65–67, 604/131, 207, 246; 128/DIG. 12, DIG. 13

(56) References Cited

U.S. PATENT DOCUMENTS

| | | | | |
|---|---|---|---|---|
| 3,739,943 A | * | 6/1973 | Wilhelmson et al. |
| 3,858,574 A | * | 1/1975 | Page |
| 3,910,257 A | * | 10/1975 | Fletcher et al. |
| 4,173,971 A | * | 11/1979 | Karz |
| 4,413,314 A | * | 11/1983 | Slater et al. |
| 4,449,538 A | * | 5/1984 | Corbitt et al. |
| 4,531,527 A | * | 7/1985 | Reinhold, Jr. et al. |
| 4,561,443 A | * | 12/1985 | Hogrefe et al. |
| 4,586,260 A | * | 5/1986 | Baxter et al. |
| 4,624,661 A | * | 11/1986 | Arimond |
| 4,676,776 A | * | 6/1987 | Howson |
| 4,696,671 A | * | 9/1987 | Epstein et al. |
| 4,731,051 A | * | 3/1988 | Fischell |
| 4,756,706 A | * | 7/1988 | Kerns et al. |
| 4,797,840 A | * | 1/1989 | Fraden |
| 4,803,625 A | * | 2/1989 | Fu et al. |
| 4,810,243 A | * | 3/1989 | Howson |
| 4,828,545 A | * | 5/1989 | Epstein et al. |
| 4,850,972 A | * | 7/1989 | Schulman et al. |
| 4,865,584 A | * | 9/1989 | Epstein et al. |
| 4,871,351 A | * | 10/1989 | Feingold |
| 4,901,221 A | * | 2/1990 | Kodosky et al. |
| 4,925,444 A | * | 5/1990 | Orkin et al. |
| 4,933,843 A | * | 6/1990 | Scheller et al. |
| 4,942,514 A | * | 7/1990 | Miyagaki et al. |

(List continued on next page.)

OTHER PUBLICATIONS

* A.H. McMorris, J.L. Kelleway, B. Tapadia and E.L. Dohmann, "Are Process Control Rooms Obsolete?", taken from Control Engineering, pp. 42–47, Jul. 1971.

(List continued on next page.)

*Primary Examiner*—Manuel Mendez
(74) *Attorney, Agent, or Firm*—Matthew J. Gryzlo; Wallenstein & Wagner

(57) ABSTRACT

A medical treatment administration system 610 for delivering a medical treatment to a patient 618. The system 610 has a medical device 612 disposed in a first location, an electronic processor 628 coupled to the medical device 612, a sensor 616 coupled to the processor 628, and a remote controller 646 disposed at a second location remote from the first location. The remote controller 646 has an input device to control operation of the electronic processor 628. The sensor 616 receives one or more signals which it transfers 624 to the processor 628. The signals can be derived from the patient's physiological condition and/or the environment of the patient. The processor 628 receives the signals and performs a calculation 630 of the signal. Based on the result of the calculation, the processor 628 regulates the distribution of medical treatment to the patient 618 over a period of time.

23 Claims, 21 Drawing Sheets

U.S. PATENT DOCUMENTS

| | | | |
|---|---|---|---|
| 4,952,928 A | * | 8/1990 | Carroll et al. |
| 4,995,268 A | * | 2/1991 | Ash et al. |
| 5,038,800 A | * | 8/1991 | Oba |
| 5,078,683 A | * | 1/1992 | Sancoff et al. |
| 5,100,380 A | * | 3/1992 | Epstein et al. |
| 5,109,849 A | * | 5/1992 | Goodman et al. |
| 5,115,133 A | * | 5/1992 | Knudson |
| 5,116,312 A | * | 5/1992 | Blankenship et al. |
| 5,137,023 A | * | 8/1992 | Mendelson et al. |
| 5,152,296 A | | 10/1992 | Simons |
| 5,153,827 A | | 10/1992 | Coutré et al. |
| 5,155,693 A | | 10/1992 | Altmayer et al. |
| 5,165,874 A | | 11/1992 | Sancoff et al. |
| 5,167,235 A | | 12/1992 | Seacord et al. |
| 5,191,891 A | | 3/1993 | Righter |
| 5,207,642 A | | 5/1993 | Orkin et al. |
| 5,213,099 A | | 5/1993 | Tripp, Jr. |
| 5,226,425 A | | 7/1993 | Righter |
| 5,230,623 A | | 7/1993 | Guthrie et al. |
| 5,256,157 A | | 10/1993 | Samiotes et al. |
| 5,291,190 A | | 3/1994 | Scarola et al. |
| 5,295,062 A | | 3/1994 | Fukushima |
| 5,297,554 A | | 3/1994 | Glynn et al. |
| 5,317,506 A | | 5/1994 | Coutré et al. |
| 5,338,157 A | | 8/1994 | Blomquist |
| 5,361,758 A | | 11/1994 | Hall et al. |
| 5,368,562 A | | 11/1994 | Blomquist et al. |
| 5,376,070 A | | 12/1994 | Purvis et al. |
| 5,378,231 A | | 1/1995 | Johnson et al. |
| 5,395,321 A | | 3/1995 | Kawahara et al. |
| 5,395,329 A | | 3/1995 | Fleischhackor et al. |
| 5,400,246 A | | 3/1995 | Wilson et al. |
| 5,412,400 A | | 5/1995 | Takahara et al. |
| 5,429,602 A | | 7/1995 | Hauser |
| 5,469,855 A | | 11/1995 | Pompei et al. |
| 5,482,446 A | | 1/1996 | Williamson et al. |
| 5,485,408 A | | 1/1996 | Blomquist |
| 5,509,422 A | | 4/1996 | Fukami |
| 5,522,396 A | | 6/1996 | Langer et al. |
| 5,544,651 A | | 8/1996 | Wilk |
| 5,558,638 A | | 9/1996 | Evers et al. |
| 5,558,640 A | | 9/1996 | Pfeiler et al. |
| 5,569,187 A | | 10/1996 | Kaiser |
| 5,573,506 A | | 11/1996 | Vasko |
| 5,582,593 A | | 12/1996 | Hultman |
| 5,609,575 A | | 3/1997 | Larson et al. |
| 5,643,212 A | | 7/1997 | Coutré et al. |
| 5,658,250 A | | 8/1997 | Blomquist et al. |
| 5,807,336 A | | 9/1998 | Russo et al. |
| 5,885,245 A | * | 3/1999 | Lynch et al. .......... 604/67 |
| 5,895,371 A | | 4/1999 | Levitas et al. |

OTHER PUBLICATIONS

* Product literature, Abbott Laboratories' LIFECARE® Blue Line System, Jul. 1990, 8 pages.
* L.C. Sheppard, "*Computer Based Clinical Systems: Automation and Integration*," taken from $39^{th}$ ACEME, Sep. 13–17, 1986; pp. 73–75.
* Deborah J. Mayhew, "*Principles and Guidelines in Software User Interface Designs*," Prentice–Hall, Inc., 1992, selected portions of Chapter 9 (17 pages).
* Jack Shandle, "*Who Will Dominate the Desktop in the '90s? IBM and Apple Rev Their Technology Engines as the Multimedia Age Begins*," Electronics, Feb. 1990, pp. 48–50.
* Ben Shneiderman, "*Designing the User Interface: Strategies for Effective Human–Computer Interaction*," Addison–Wesley Publishing Company, 1002, Chapter 5: Direct Manipulation (56 pages).
* Product literature, Baxter Healthcare Corporation, "MultiPlex™ Series 100 Fluid Management System," copyrighted 1988, 2 pages.
* Product literature, Baxter Healthcare Corporation, MultiPlex™ Series 100 Fluid Management System, undated, 2 pages.
* Product literature, Baxter Healthcare Corporation, Flo–Gard® 6201 Volumetric Infusion Pump, copyrighted 1992, 2 pages.
* Literature of I–Flow Corporation advertising its Vivus 4000™ Infusion System; presentation materials, Eric W. Brown, "*Trends in Complex I.V. Therapies for the Home Infusion Market*," presented at Advances in Drug Delivery, Dallas, Texas, Dec. 7, 1988, 10 pages.
* Jerry Hirsch, "*Portable IV Frees Patients*," The Orange County Register, Nov. 21, 1991, 1 page.
* Marshall D. Bedder, et al., entitled "*Cost Analysis of Two Implantable Narcotic Delivery Systems*," Journal of Pain And Symptom Management, vol. 6, No. 6, Aug. 1991, pp. 368–373.
* Peter Lord, et al., "*MiniMed Technologies Programmable Implantable Infusion System*," Annals New York Academy of Sciences, pp. 66–71, describing clinical trials from Nov., 1986.
* Brochure, "IMED®STATUS™ Infusion Management System," (undated, 6 pages).
* "*IEEE–488 and VXIbus Control, Data Acquisition, and Analysis . . . the Most Choices*," select pages taken from National Instruments, Application Software Products And Application Software Overview, (1991) 17 pages.
* "LabVIEW® User Manual; Chapter 2, The Front Panel" taken from National Instruments Corporation, Jan., 1990; pp. 1–36.
* J.C Crone, Jaromir Belic and Roger W. Jelliffee, M.D., "*A Programmable Infusion Pump Controller*," taken from 30 Annual Conference on Engineering in Medicine and Biology, Nov. 5–9, 1977; pp. A–35826 through A–35837.
* "BLOCK *Medical: Growing With Home Infusion Therapy*," taken from INVIVO, The Business And Medicine Report, Apr., 1991; pp. 7–9.
* Selected pages from Chapters 1 and 2 by Foley, et al., "*Fundamentals of Interactive Computer Graphics*," 1982.
* James D. Foley and Andries Van Dam, "*Fundamentals of Interactive Computer Graphics*," Addison–Wesley Publishing Company, 1982, selected pages from Chapters 1 and 2 (11 pages).
* Supplemental FDA 510K Notification dated Nov. 9, 1995 by Sabratek Corporation regarding Sabratek's 3030 Infusion Pump and Sabratek's Communication Link Software Package.
* Response of Sabratek Corporation dated Mar. 5, 1996 to FDA request for additional information, 8 pages.

* cited by examiner

MEDICAL APPARATUS WITH REMOTE CONTROL

RELATED REFERENCES

This application is a continuation-in-part of U.S. application Ser. No. 09/272,502, filed Mar. 19, 1999 now abandoned, which is a continuation of application Ser. No. 08/951,976, filed Oct. 16, 1997, now U.S. Pat. No. 5,885,245, which is a continuation-in-part of U.S. application Ser. No. 08/691,687, filed Aug. 2, 1996 (now abandoned), which are expressly incorporated herein by reference and made a part hereof.

TECHNICAL FIELD

The present invention is directed to an apparatus for monitoring and/or controlling a medical device, such as an infusion pump, from a remote location.

BACKGROUND OF INVENTION

An infusion pump is used to automatically administer liquid medicant to a patient. The liquid medicant is supplied from a source of medicant and pumped into the patient via a catheter or other injection device. The manner in which the liquid is infused is controlled by the infusion pump, which may have various modes of infusion, such as a continuous mode in which the liquid medicant is continuously infused at a constant rate, or a ramp mode in which the rate of infusion gradually increases, then remains constant, and then gradually decreases.

Typically, the monitoring of an infusion pump is performed by reviewing a visual display means incorporated in the infusion pump, and the control of the infusion pump is performed by activating an input device, such as a keypad, incorporated with the infusion pump. Consequently, the monitoring and/or control of an infusion pump is performed at the same location at which the infusion pump is disposed.

Additionally, for many types of medical treatments, the impact and ultimate usefulness of the treatment depends on the patient's tolerability and sensitivity to the treatment. Such measures assist physicians in accurately and efficiently treating patients. To date, however, most medical treatments are provided to the patient based on objective measurements, rather than on actual measurements of the specific subject or environment of the subject.

For example, typical medical treatment parameters for many drug therapies are provided based on the generic circadian system. Under the circadian system it has been know in the medical industry that typical biological functions of plants and animals reoccur at approximately 24-hour intervals. In humans, the body's clock is located in the suprachiasmatic nucleus (SCN), a distinct group of cells found within the hypothalamus. The SCN controls or coordinates the circadian rhythm in the human body. Typically, a human's circadian rhythm is calibrated by the alternation of light through the eyes and darkness via melatonin secretion by the pineal gland.

Furthermore, the cellular metabolism and proliferation in normal human tissues display similar rhythms, and thus have predictable amplitudes and times of peak and trough. Such rhythms influence drug pharmacology, tolerability, and ultimate usefulness. For example, it has been thought that the circadian rhythm influences the uses and effects of anti-cancer medication, including tolerability and anti-tumor efficacy in cancer treatment. Therefore, in chronopharmacologic intervention, anti-cancer drugs are delivered according to a standard circadian rhythm, especially with chemotherapy. For example, Floxuridine delivery is typically given in four doses, each dose dependent on the time of the day:

14% of dose between 9 am and 3 pm;

68% of dose between 3 pm and 9 pm;

14% of dose between 9 pm and 3 am; and,

4% of dose between 3 am and 9 am.

Generally, the time at which the medication is delivered is selected by the physician to objectively coincide with changes in the patient's metabolism. However, the circadian rhythm is merely an estimate of the changes in the patient's metabolism, and is not based on the actual patient's metabolism. Thus, whether the medication delivery actually coincides with the patient's actual metabolism is neither evaluated nor determined.

Additionally, different medical treatments have different optimum dosing time-profiles. For example, different anti-tumor drugs are typically dosed at different times: Epirubicin and Daunorubicin are typically dosed at 2 hours after light onset; Cyclophasphamide is typically dosed at 12 hours after light onset; Cisplatin is typically dosed at 15 hours after light onset; and, Vinblastine is typically dosed at 18 hours after light onset. As can be seen, different drugs have different mechanisms of action.

Other factors, however, may also affect proper medical treatment. For example, the minimum sensitivity of normal tissue is thought to be related to the enzyme levels that affect drug metabolism (e.g., glutathione). An overall driver of these variables is thought to be the rest-activity cycle of the patient. Because of this effect, it is known that laboratory rat studies should be conducted with the animal subjected to a 12 hour light, and 12 hour dark cycle.

Nevertheless, it is known that different patients, and with regard to cancer treatment, even different tumors, are not all on the same circadian cycle. Thus, there are at least two aspects one needs to optimize during circadian therapy: (1) the peak sensitivity of the tumor(s); and, (2) the minimum sensitivity of the normal tissues.

Standard chronopharmacologic intervention takes advantage of the circadian rhythm in drug tolerability by controlling the timing and dosing. Thus, it can reduce the effect of toxicity and improve the quality of life for the patient. Furthermore, with many drugs, including chemotherapy drugs, by administering a higher maximum tolerated dose at the least toxic circadian time, an improvement in survival may be derived. However, as explained above, there are numerous flaws with providing medical treatments following the standard circadian system.

SUMMARY OF THE INVENTION

According to one aspect of the present invention, the medical apparatus has a programmable medical device for administering a medical treatment to a patient, the programmable medical device being disposed at a first location, and a remote controller for controlling the programmable medical device, the remote controller being disposed at a second location remote from the first location at which the programmable medical device is disposed. The programmable medical device includes means for administering the medical treatment to the patient and an input device for allowing a user to input control commands to control the administering means. The remote controller includes a display device, means operatively coupled to the display device for generating a visual display of a virtual input device substantially corresponding to the input device of the programmable medical device, and means for allowing a user at the second location to activate the virtual input device to allow the user to control the operation of the programmable medical device from the second location.

The input device may be, for example, a keypad, and the virtual input device may be a visual display of a plurality of keys having substantially the same configuration as the keypad.

The programmable medical device may be an infusion pump for administering a liquid medicant to a patient, which includes a liquid injection device adapted to be connected to the patient, a conduit connected to the liquid injection device, a pumping mechanism for pumping the liquid medicant through the conduit and into the patient via the liquid injection device, and a controller for controlling the pumping mechanism.

According to another aspect of the present invention, the medical treatment device has a supply of medication and a means for delivering the medication to the patient using a control algorithm and a sensing device. The control algorithm is coupled to the medical device. The sensing device is coupled to the control algorithm and the sensing device sends a signal to the control algorithm. The control algorithm processes the signal received from the sensing device and develops a feedback control based on a result of processing the signal to determine whether medication should be delivered from the medical treatment device to the patient. The feedback control is provided to the medical treatment device to control the delivery of the medical treatment to the patient. The remote controller for the device is disposed at a second location remote from the first location. The remote controller has an input device to control operation of the control algorithm.

According to yet another aspect of the present invention, the medication delivery system of the present invention comprises a programmable medical device, a local controller, and a remote controller. The programmable medical device is located at a first location for administering a medical treatment to a patient, and the programmable medical device has a means for administering the medical treatment to the patient. Additionally, the programmable medical device has a first input device for entering control commands for the programmable medical device. The local controller is operatively connected to the programmable medical device. The local controller is disposed at the first location and has a second input device for entering control commands for the local controller. Additionally, the local controller is operatively connected to the patient to receive a signal from the patient, and the local controller manipulates operation of the programmable medical device. The remote controller is disposed at a second location remote from the first location at which the programmable medical device is disposed, and has means to allow a user at the second location to control the local controller.

These and other features and advantages of the present invention will be apparent to those of ordinary skill in the art in view of the detailed description of the preferred embodiment, which is made with reference to the drawings, a brief description of which is provided below.

BRIEF DESCRIPTION OF DRAWINGS

FIG. 15 is an illustration of a graphical user menu that may be displayed by the remote monitor/controller;

DETAILED DESCRIPTION OF PREFERRED EMBODIMENT

Figure 1:
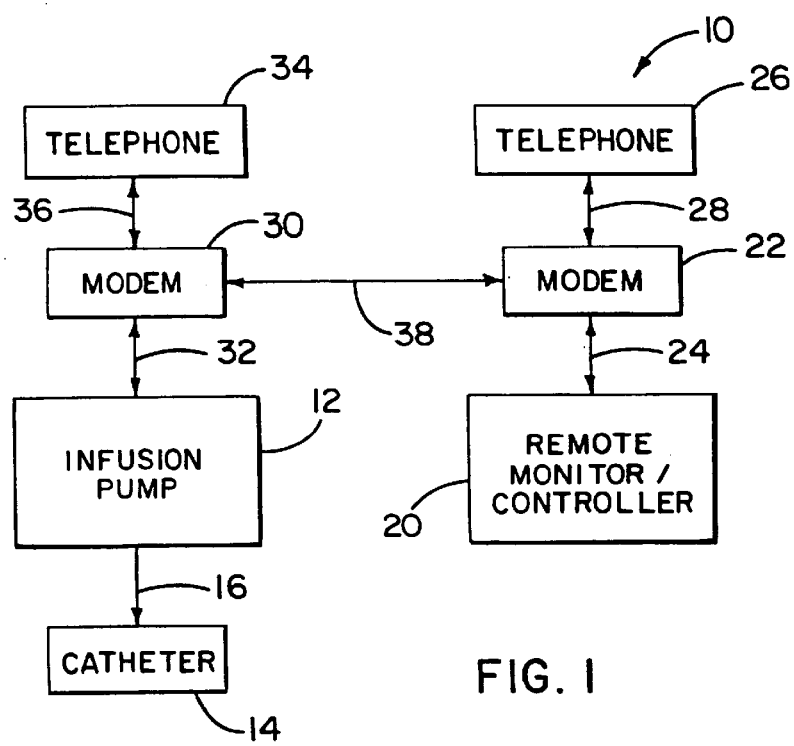
FIG. 1 is a block diagram of an apparatus for administering medical treatment to a patient and monitoring the condition of the patient.

FIG. 1 illustrates one embodiment of an apparatus 10 for administering medical treatment to a patient. Referring to FIG. 1, the apparatus 10 includes a programmable medical treatment means in the form of an infusion pump 12, which is connected to a liquid medicant injection device in the form of a catheter 14 via a liquid conduit schematically shown as 16.

The apparatus 10 includes a remote monitor/controller 20 which is disposed at a room location remote from the room location at which the infusion pump 12 is located. The remote monitor/controller 20 could be disposed in a different room of the same building in which the pump 12 is disposed, or in a different building than the one in which the pump 12 is disposed. The remote monitor/controller 20 is connected to a conventional voice/data modem 22 via a data link 24, and the modem 22 is also connected to a telephone 26 via a voice link 28. The infusion pump 12 is connected to a conventional voice/data modem 30 via a data link 32, and the modem 30 is connected to a telephone 34 via a voice link 36. The two modems 22, 30 are interconnected to bidirectional voice and data communication via a communication link 38, which could be a telephone line, for example.

Figure 2:
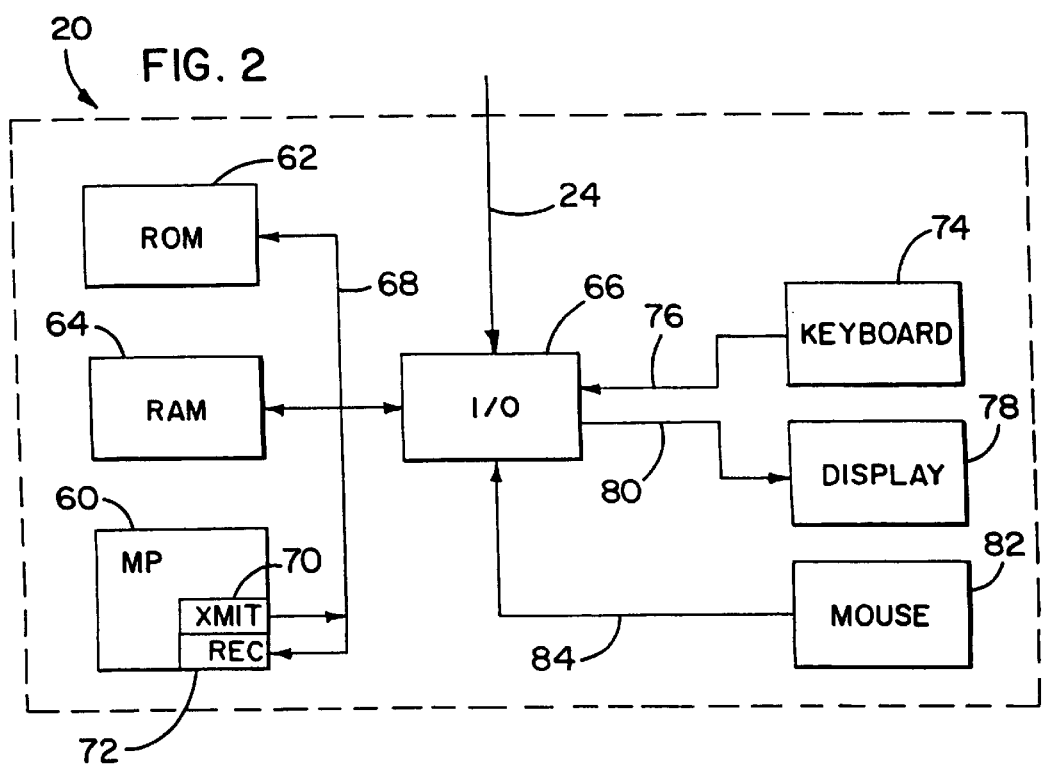
FIG. 2 is a block diagram of the electronic components of the remote monitor/controller shown schematically in FIG. 1.

FIG. 2 is a block diagram of the electronics of the remote monitor/controller 20 shown schematically in FIG. 1. Referring to FIG. 2, the remote monitor/controller 20 includes a microprocessor (MP) 60, a read-only memory (ROM) 62, a random-access memory (RAM) 64, and an input/output (I/O) circuit 66, all of which are interconnected by an address/data bus 68. The microprocessor 60 has a transmit buffer (XMIT) 70 for transmitting data bytes and a receive buffer (REC) 72 for receiving data bytes. The remote monitor/controller 20 has a keyboard 74 connected to the I/O circuit 66 via a line 76, a display device 78, such as a CRT, connected to the I/O circuit 66 via a line 80, and an input device, such as an electronic mouse 82, connected to the I/O circuit 66 via a line 84. The remote monitor/controller 20 can also include one or more disk drives, such as a hard disk drive or a floppy disk drive.

Figure 3:
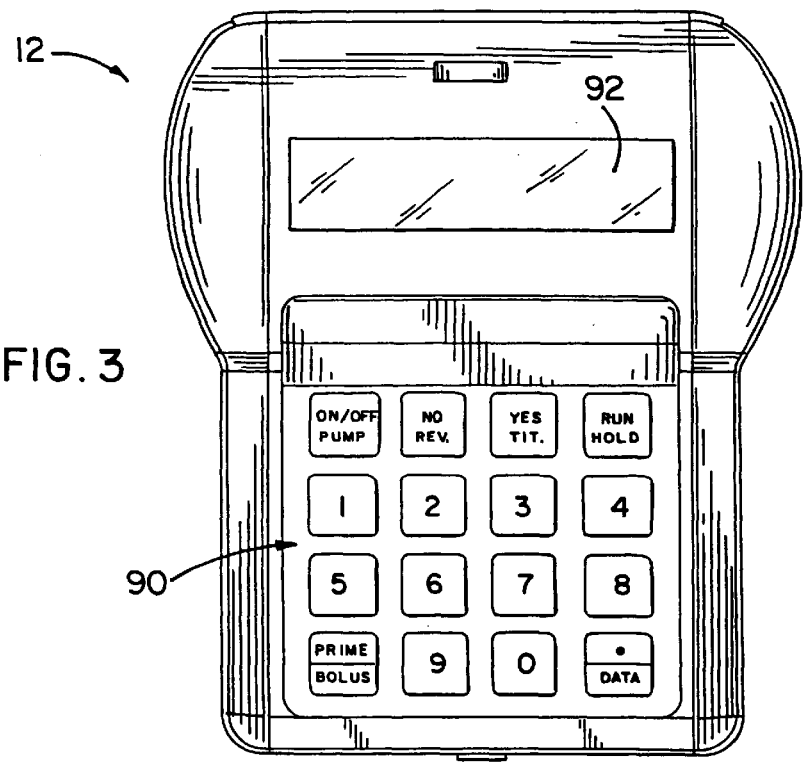
FIG. 3 is a front view of one embodiment of the infusion pump shown schematically in FIG. 1.

FIG. 3 is a front view of one embodiment of the infusion pump 12 shown schematically in FIG. 1. Referring to FIG. 3, the pump 12 has an input device in the form of a keypad 90 via which a user may input data and commands and a display 92 for displaying textual messages to the user.

Figure 4:
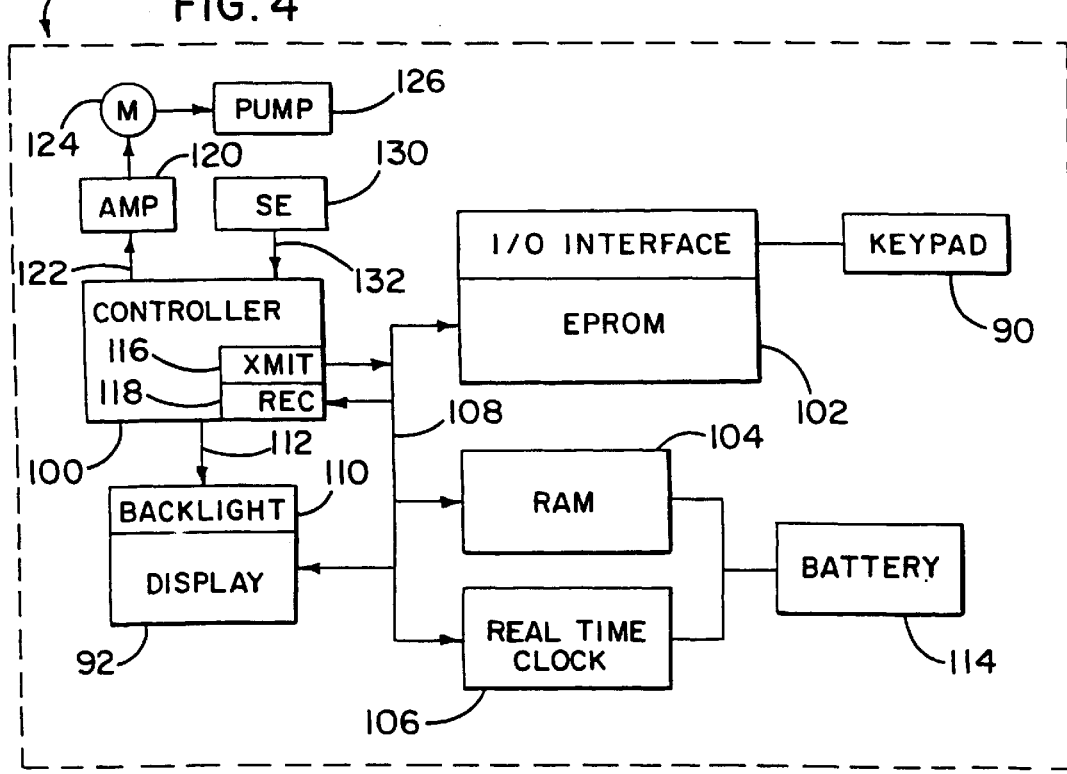
FIG. 4 is a block diagram of the electronic components of the infusion pump of FIG. 3.

A block diagram of the electronics of the infusion pump 12 is shown in FIG. 4. Referring to FIG. 4, the pump 12 includes a controller 100, an electrically programmable read-only memory (EPROM) 102 having a built-in I/O interface 102a, a nonvolatile RAM 104, a real-time clock 106 and the display 92, all of which are interconnected by a communications bus 108. The display 92 has a backlight 110 which is selectively activated by an enable signal generated on a line 112 interconnecting the controller 100 and the backlight 110. Both the RAM 104 and the real-time clock 106 are connected to a battery 114 which supplies power to them only in the absence of system power. The controller 100 has a transmit buffer 116 and a receive buffer 118 connected to the communications bus 108.

The controller 100 controls the medicant infusion rate by periodically transmitting a control signal to an amplifier circuit 120 via a line 122 to drive a pump motor 124 which drives a pumping mechanism 126, such as a rotary pump wheel (not shown) adapted to make contact with a portion of the liquid conduit 16 (FIG. 1) connected to the catheter 14.

The controller 100 receives periodic inputs from a shaft encoder (SE) sensor 130, which is disposed on the shaft of the motor 124. The SE sensor 130 may be a two-phase motion sensing encoder which provides two signal outputs to the controller 100. The rotational speed of the motor 124 and its direction of rotation are determined by the controller 100 based upon the rate and phase relationship between the two signal outputs.

The SE encoder 130 periodically transmits the signals to the controller 100 via a line 132. Each time the signals are transmitted, an interrupt is generated, and the controller 100 compares the actual position of the motor shaft with its desired position, and transmits a new control signal, such as a pulse-width modulated signal, to the amplifier 120 via the line 122 to ensure that the actual speed of the motor 124 corresponds to the motor speed required for the desired medicant infusion rate. The interrupts caused by the SE sensor 130 are assigned to the highest priority so that they are responded to immediately, before any other actions are taken by the controller 100.

The pump 12 has a number of other features not described herein, which are disclosed in the following patent applications, each of which is incorporated herein by reference: U.S. Ser. No. 08/399,184, filed Mar. 6, 1995, entitled "Infusion Pump Having Power Saving Modes"; U.S. Ser. No. 08/398,977, filed Mar. 6, 1995, entitled "Infusion Pump With Selective Backlight"; U.S. Ser. No. 08/398,980, filed Mar. 6, 1995, entitled "Infusion Pump With Different Operating Modes"; U.S. Ser. No. 08/398,886, filed Mar. 6, 1995, entitled "Cassette For An Infusion Pump; U.S. Ser. No. 08/399,183, filed Mar. 6, 1995, entitled "Infusion Pump With Dual-Latching Mechanism"; U.S. Ser. No. 08/398,887, filed Mar. 6, 1995, entitled "Infusion Pump With Historical Data Recording."

Figure 5:
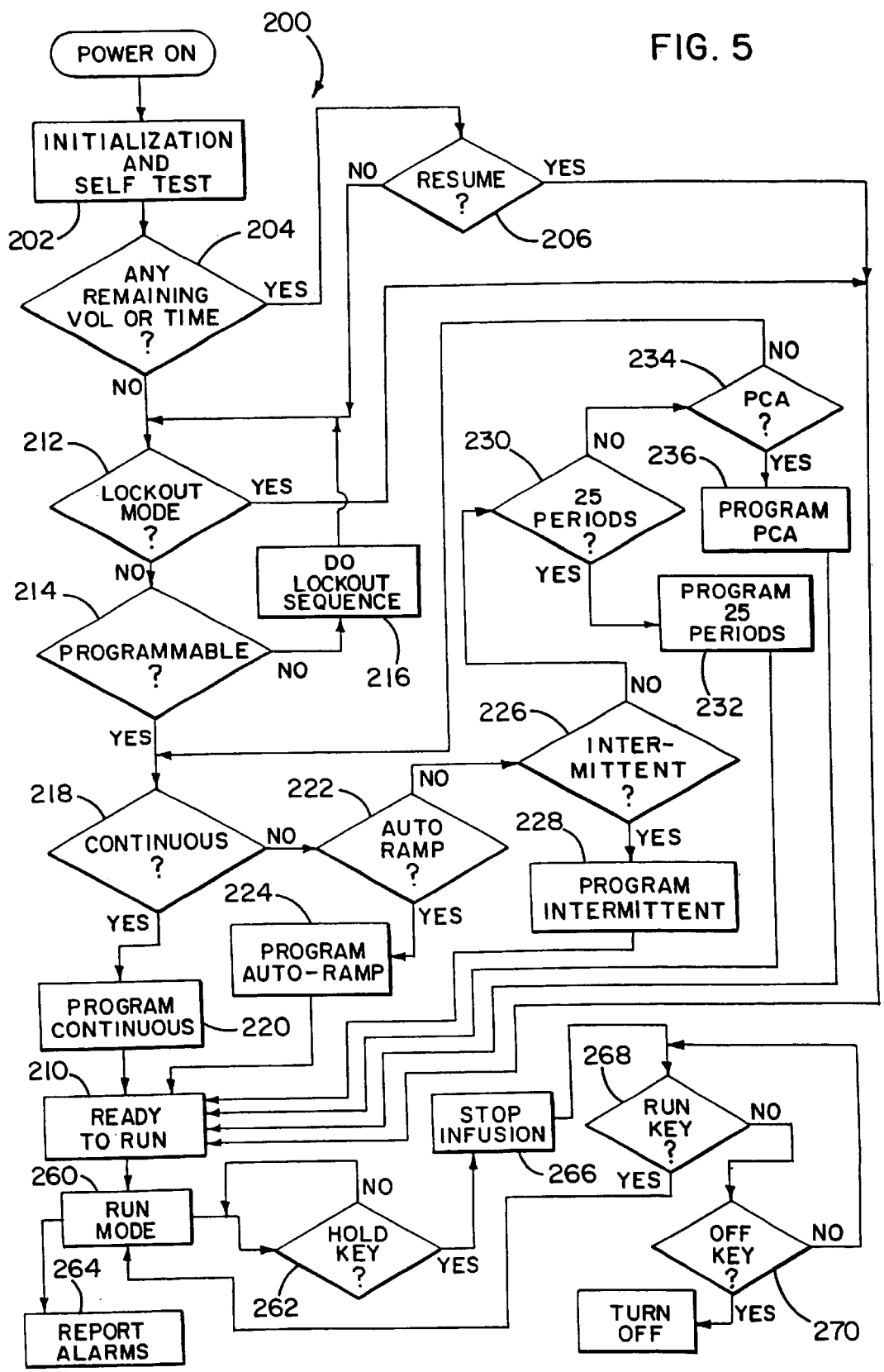
FIG. 5 is a flowchart of the overall operation of the infusion pump.

The operation of the infusion pump 12 is controlled by a computer program stored in the EPROM 104 and executed by the controller 100. A flowchart 200 of the overall operation is illustrated in FIG. 5. Referring to FIG. 5, when the pump 12 is turned on, at step 202 the pump is initialized and a test of the pump operation is performed. The pump 12 may be turned off temporarily during an infusion, in which case the pump 12 may continue the infusion when it is turned back on, as described below. At step 204, if there is any remaining volume of liquid to be infused by the pump or any additional time remaining for an infusion, which would be the case where the pump was temporarily turned off during an infusion, the program branches to step 206, where the user is asked, via a message displayed on the display 92, whether the previous infusion should be resumed. If the user answers yes (via the keypad 90), the program branches to a ready-to-run step 210. If the previous infusion is not to be resumed, the program branches to step 212.

The infusion pump 12 has a lockout mode in which the user may be prevented from programming the infusion parameters, such as the volume to be infused or the rate of infusion. For example, the pump 12 could be programmed by a medical assistant to deliver a particular infusion having a particular flow profile, flow rate and volume to be infused. After programming that infusion, the medical assistant could place the pump in lockout mode, which would prevent the patient from changing any of the infusion parameters. At step 212, if the pump 12 has been previously placed in lockout mode, the program branches directly to the ready-to-run step 210, bypassing all programming steps.

At step 212, if the pump is not in lockout mode, the program branches to step 214, at which point the program prompts the user, via the display 92, to input whether the patient should be allowed to program the pump during the subsequent infusion. If the pump is not to be programmable, the program branches to step 216 where a lockout sequence is performed by requesting the user to input which infusion modes should be locked out. If the pump is to be programmable by the patient, the program bypasses step 216.

The infusion pump 12 has five basic modes of infusion: 1) a continuous mode in which the pump delivers a single volume at a single rate; 2) an auto-ramp mode in which the pump delivers liquid at a rate that gradually increases to a threshold rate, stays constant at the threshold rate, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain-controlled analgesic (PCA) mode during which the pump will periodically infuse boluses of analgesic in response to periodic requests by the patient.

At step 218, the pump 12 generates on the display 92 the prompt "Continuous" to the user. If the user desires to use the pump in its continuous mode, the user answers "yes" via the keypad 90, and the program branches to step 220 at which the continuous mode is programmed by the user by entering a number of infusion parameters, such as the desired infusion rate, the volume to be infused, etc. At step 218, if the user does not want to use the continuous mode, the user answers "No," and the program branches to step 222. Steps 222–236 are generally the same as steps 218 and 220, except that the user may be prompted for different infusion parameters, depending on which of the five possible infusion modes is selected.

After the completion of one of the steps 220, 224, 228, 232, or 236, the program branches to the ready-to-run step 210. When the user presses the "Run" key, the pump 12 enters the run mode 260 and infuses the patient with a liquid medicant in accordance with the infusion mode selected at one of steps 218, 222, 226, 230, 234 and the infusion parameters entered at one of steps 220, 224, 228, 232, 236. The pump 12 remains in the run mode 260 until the "Hold" key is pressed, as determined at step 262. Upon the occurrence of an alarm condition, an alarm is reported at step 264. At step 262, if the hold key is pressed, the infusion is stopped at step 266, and the pump 12 waits for the run key to be pressed at step 268 or the on/off switch to be turned off at step 270.

Summarizing the operation described above, if the pump is to be utilized in lockout mode, a medical assistant turns the pump on, programs the desired infusion mode at one of steps 220, 224, 228, 232, 236, and then turns the pump off. The programmed infusion parameters will be retained in the memory 104. The medical assistant would then turn the pump back on, press the "No" key in response to the "Programmable" prompt at step 214, enter the lockout information at step 216, and then turn the pump off again. When the patient subsequently turned on the pump to perform the infusion, the program would proceed from step 212 directly to the ready-to-run step 210, which would prevent the patient from altering the infusion parameters.

If the lockout mode was not utilized, the medical assistant or the patient could turn the pump on, program the desired infusion mode, and then press the "Run" key to start the infusion without ever turning the pump off.

During programming and operation, the infusion pump 12 automatically records in the non-volatile memory 104 all significant infusion data to generate a complete historical data record which can be later retrieved from the memory 104 and used for various purposes, including clinical purposes to aid in determining how effective a particular infusion therapy was and treatment purposes to confirm that the prescribed infusion was actually delivered.

Figure 6:
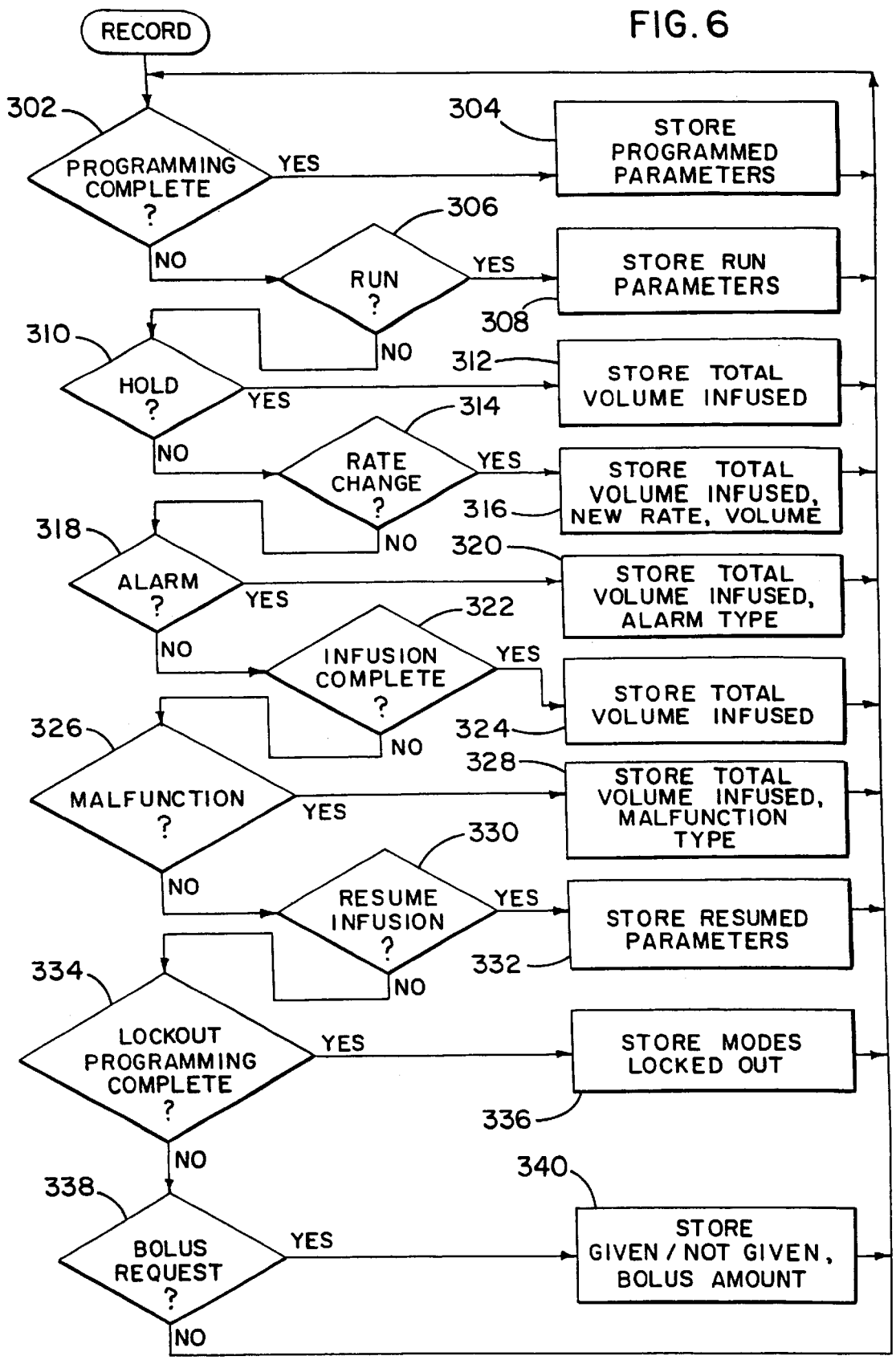
FIG. 6 illustrates a number of data-recording steps performed during the operation of the infusion pump.

FIG. 6 illustrates various steps at which infusion data is recorded that are performed during the overall pump operation shown generally in FIG. 5. The infusion data recorded in the memory 104 is set forth in Table 1 below. A number of events which trigger the storage of data are listed in the left-hand column of Table 1, and the infusion data that is recorded upon the occurrence of each event is listed in the right-hand column of Table 1. The time at which the infusion data is recorded, which is determined by the real-time clock 106, is also stored along with the infusion data.

TABLE 1

| EVENT | DATA RECORDED |
|---|---|
| Power On | Date and Time |
| Program | Infusion parameters. See Table 2 |
| Run | Infusion parameters. See Table 2. |
| Hold | Total Volume Infused |
| Restart | Time of Restart |
| Rate Changes | Total Volume Infused, Rate, Volume |
| Alarms | Total Volume Infused, Alarm Type |
| Infusion Complete | Total Volume Infused |
| Malfunctions | Total Volume Infused, Malfunction Type |
| Resume | Infusion parameters. See Table 2. |
| Maintenance Date | Date |
| Patient ID | Patient ID Number |
| Serial No. | Serial Number |
| Language Change | New Language |
| Lockout | Modes Locked Out |
| Pressure Select | New Pressure Setting |
| Bolus Request | Given/Not Given, Bolus Amount |
| Titration | New Parameters |
| Power Off | Time of Power Off |
| Version No. | Software Version Number |

Referring to Table 1 and FIG. 6, when the power to the infusion pump 12 is turned on, the date and time of the power turn-on is recorded. When the pump is completely programmed pursuant to one of steps 220, 224, 228, 232, 236 (FIG. 5) as determined at step 302, the programmed infusion parameters are stored at step 304, along with the time of such storage. The particular parameters that are stored depend upon which infusion mode was programmed. Several examples of infusion parameters that are stored for each of a number of infusion modes are illustrated in Table 2 set forth below.

TABLE 2

| INFUSION MODE | INFUSION PARAMETERS |
|---|---|
| Continuous | Infusion Mode |
|  | Infusion Rate |
|  | Volume To Be Infused |
|  | Delay Time |
|  | Total Bag Volume |
|  | KVO Rate |
| Auto-Ramp | Infusion Mode |
|  | Infusion Rate |
|  | Volume To Be Infused |
|  | Delay Time |
|  | Total Bag Volume |
|  | Duration of Up-Ramp |
|  | Duration of Down-Ramp |
|  | KVO Rate |
| Intermittent | Infusion Mode |
|  | Total Infusion Time |
|  | Number of Doses |
|  | Dose Time |
|  | Dose Volume |
|  | KVO Rate |

When the pump enters the run mode 260 (FIG. 5) as determined at step 306, the time at which the run mode was begun, along with the parameters pursuant to which the infusion is performed, are stored at step 308.

At step 310, if the hold key is pressed, then the time at which the hold key was pressed along with the total volume infused at the time the hold key was pressed are stored at step 312. The pump also stores any infusion rate changes, such as changes caused by switching from a continuous rate to a keep-vein-open (KVO) rate, or in the intermittent mode, changing from a KVO rate to a higher infusion rate, the presence of which are detected at step 314. The new rate and the time at which the new rate started are stored at step 316.

At step 318, if any alarms are generated, the alarm type, the time at which the alarm occurred, and the total volume infused at the time of the alarm are recorded at step 320. If the infusion is completed as determined at step 322, the program branches to step 324 where the time at which the infusion was completed is stored along with the total volume infused. At step 326, if there is a malfunction, the malfunction type, the time at which the malfunction occurred, and the total volume infused at the time of the malfunction are recorded at step 328.

At step 330, if the infusion is resumed (when the pump is turned back on after having been turned off during an infusion), the time at which the infusion is resumed along with the infusion parameters are stored at step 332. Upon the completion of the programming of a lockout sequence as determined at step 334 (i.e. after step 216 of FIG. 5), the time at which the programming of the lockout was completed is stored along with the infusion modes that were locked out. At step 338, upon the detection of a bolus request, the time at which the bolus was requested is stored at step 340, along with an indication whether the bolus was actually given and the amount of the bolus.

Figure 7:
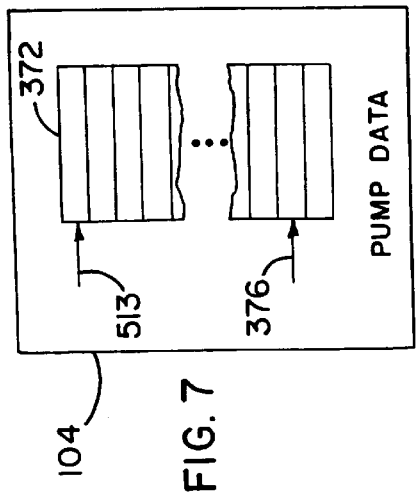
FIG. 7 is a representation of a portion of the memory of the infusion pump.

FIG. 7 illustrates the data organization of a portion of the RAM 104 in which infusion data (the data stored during the steps of FIG. 6) is stored. Referring to FIG. 7, the infusion data is stored in a number of memory locations 372. Data may be written to the memory locations 372 utilizing a pointer 376 which specifies the memory location at which data should be next stored.

Figure 8:
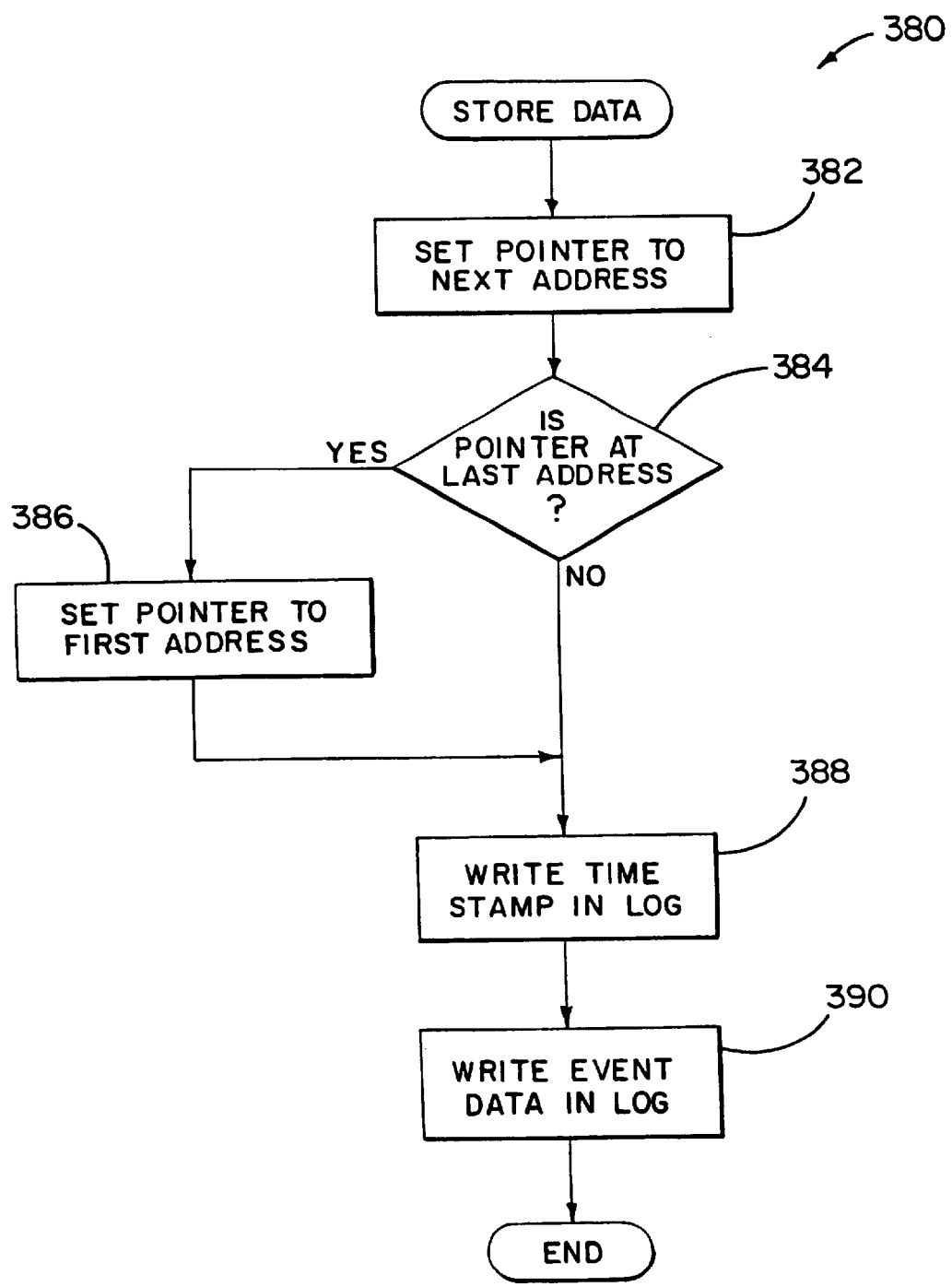
FIG. 8 is a flowchart of a store data routine which can be used to store data relating to the operation of the infusion pump and data relating to the condition of a patient.

FIG. 8 is a flowchart of a routine 380 for storing data in the memory locations 372. Referring to FIG. 8, at step 382 the pointer 376 is set to the address of the next memory location 372 in which data is to be stored. At step 384, if the pointer 376 is at the last memory location in which data may be stored, the routine branches to step 386 where the pointer is set to the address of the first memory location in which data may be stored. As a consequence of steps 384, 386, the contents of the memory locations 372 are periodically overwritten with new data; however, the number of memory locations 372 is sufficiently large so that several months of data, for example, is stored before being overwritten. At steps 388 and 390 the data is stored in the memory location 372 specified by the pointer 376 (the data includes a time stamp generated from the real-time clock 106 and event data specifying the particular infusion event).

Figure 9:
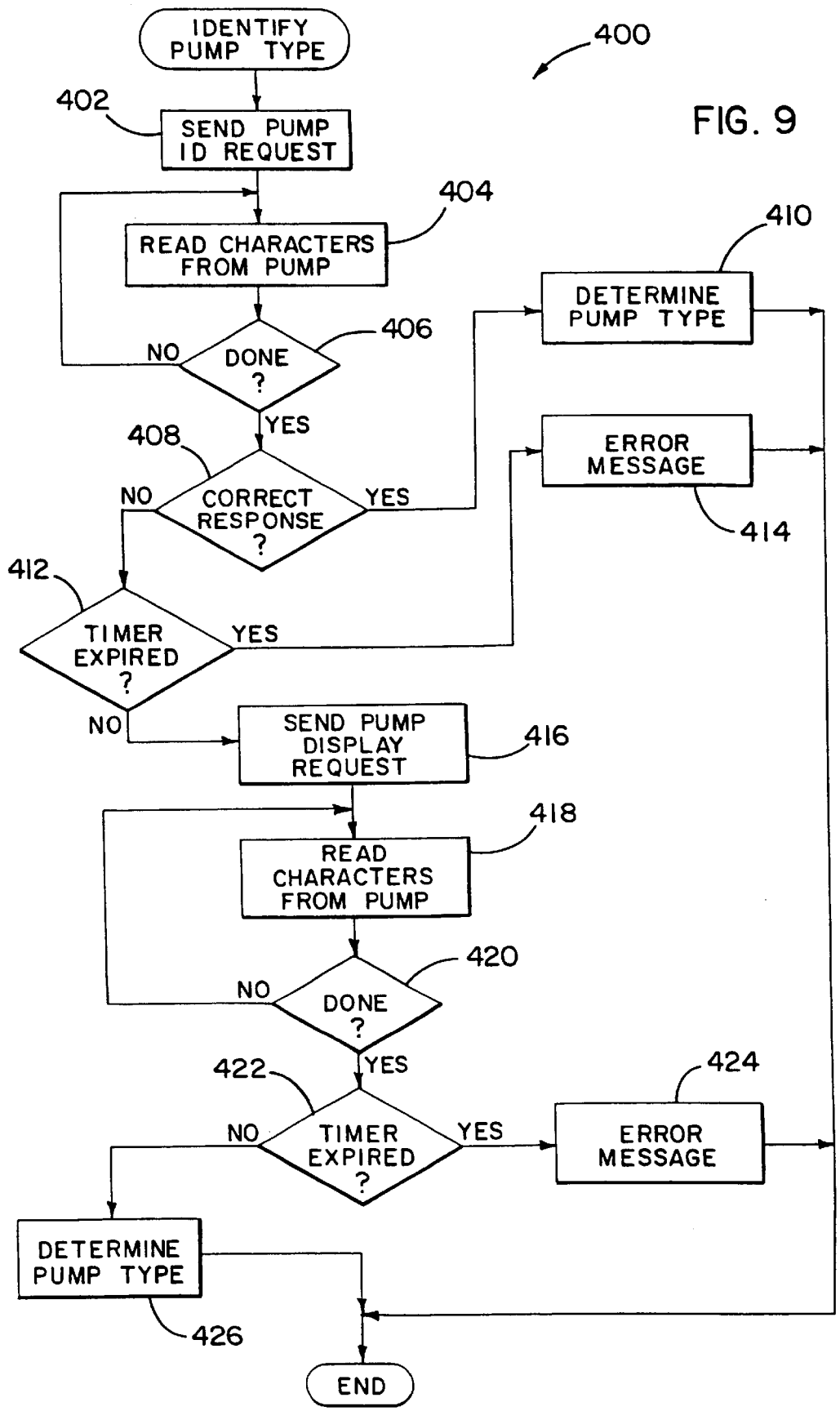
FIG. 9 is a flowchart of a routine which may be used to identify the type of infusion pump to which the remote monitor/controller is coupled.
Figure 10:
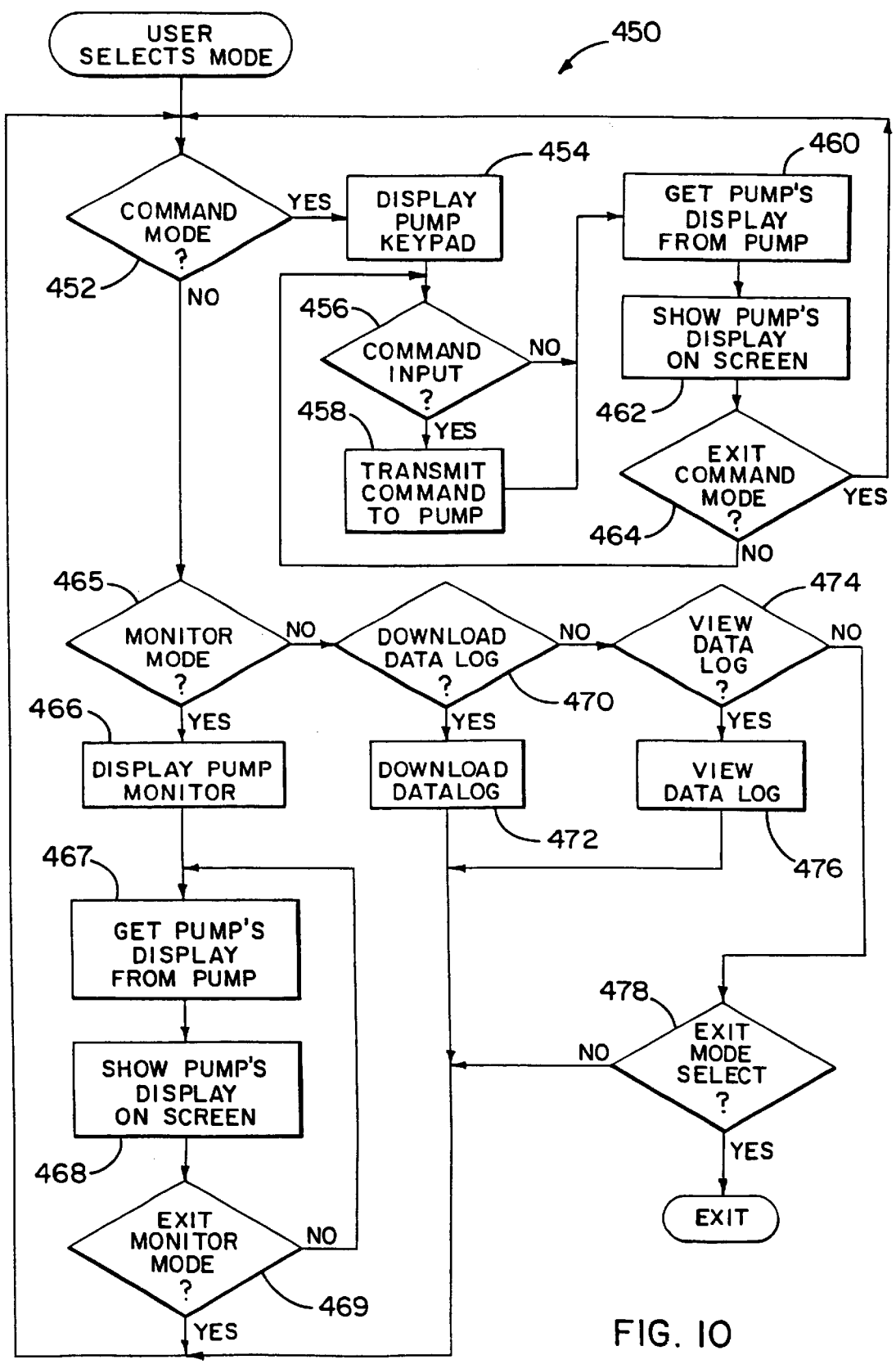
FIG. 10 is a flowchart of a mode select routine of the remote monitor/controller.
Figure 12:
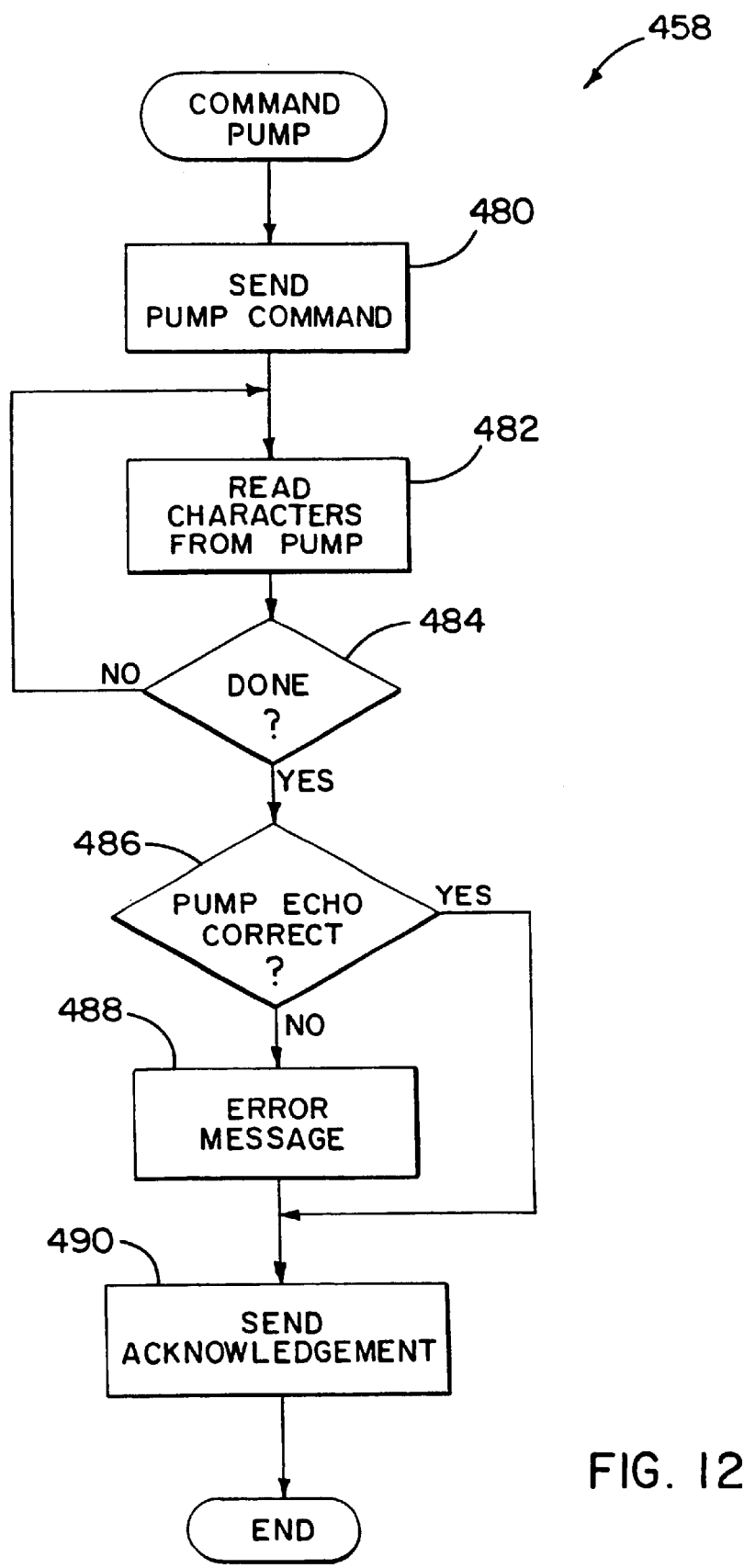
FIG. 12 is a flowchart of a command pump routine that is performed by the remote monitor/controller.

FIGS. 9, 10, and 12 are flowcharts of various routines that are performed by the remote monitor/controller 20. As described in more detail below, the remote monitor/controller 20 may be used to monitor the operation of the infusion pump 12, to control the operation of the infusion pump 12, and/or to transfer infusion data and patient data from the infusion pump 12 so that such data can be reviewed by a health care professional at a location remote from the patient.

The remote monitor/controller 20 is designed to interface with different types of infusion pumps. In order to determine which type of infusion pump the remote monitor/controller 20 is operatively coupled, a pump identification routine 400 performed after the communication link between the remote monitor/controller 20 and the infusion pump 12 is established. Referring to FIG. 9, at step 402 the remote monitor/controller 20 transmits a pump identification (ID) request to the infusion pump 12 via the communication link 38. In response to the pump ID request, the pump 12 transmits a multi-character ID code back to the remote monitor/controller 20. The ID code may include, for example, one or more characters identifying the pump model and/or one or more characters identifying the software version of the pump. At step 404, the remote monitor/controller 20 reads the characters sent from the pump 12 until all characters are received as determined at step 406 or until a predetermined time period, e.g. five seconds, elapses. The time period may be determined by a timer (not shown). The remote monitor/controller 20 may determine that all characters have been received by, for example, identifying one or more termination characters, such as a carriage-return character <CR> followed by a line-feed character <LF>.

Step 408 determines whether a correct response was received from the pump 12, which may be determined checking the characters received from the pump 12 against a list of possible ID codes. If a correct response was received, the routine branches to step 410 where the pump type is determined, for example, by comparing the received pump ID code with at least one possible ID code which identifies a particular type of infusion pump, or by comparing the received pump ID code with a number of possible ID codes, each of which identifies a particular type of infusion pump. As used herein, the "type" of infusion pump may relate to the model of the pump or the software version of the pump.

If a correct response was not received as determined by step 408, at step 412 the routine determines whether the predetermined time period measured by the timer has expired prior to receiving a termination character. If so, the routine branches to step 414 where an error message is generated due to the pump's failure to respond to the pump ID request.

At step 412, if some type of response (not a correct response) was received before the timer expired, the routine branches to step 416. Steps 416–426 comprise a second way of determining the type of infusion pump 12 connected to the remote monitor/controller 20, which is based on the number of characters in the display 92 of the pump 12. For example, a first type of infusion pump may have a display capable of displaying 12 characters, whereas a second type of infusion pump may have a display capable of displaying 32 characters. Steps 416–426 determine the type of infusion pump based on the number of characters in the display.

At step 416, the remote monitor/controller 20 transmits a pump display request to the infusion pump 12 to request the pump 12 to transmit the content of its display 92. At step 418, the remote monitor/controller 20 reads the display characters transmitted from the pump 12. At step 420, if a predetermined period of time has elapsed or if a terminating character is received, the routine branches to step 422. At step 422, if the predetermined time period measured by the timer elapsed prior to the receipt of a terminating character, the routine branches to step 424 where an appropriate error message is generated. At step 426, the type of pump is determined based on the number of display characters that were received.

The routine could also exit step 420 if a predetermined number of characters are received. In that case, where the remote monitor/controller 20 was designed to interface with two different types of infusion pumps, one having a display capability of 12 characters and another having a display capability of 32 characters, if the remote monitor/controller 20 received more than 12 display characters at step 420, it would immediately be able to determine that the pump type corresponded to a pump with a 32-character display capability.

The remote monitor/controller 20 allows four basic functions to be performed, including controlling the infusion pump 12, monitoring the operation of the pump 12, transferring infusion data from the pump 12 to the remote monitor/controller 20, and viewing the data. The user may perform one of those functions by selecting an operational mode displayed on the display device 78 (FIG. 2) of the remote monitor/controller 20 via the mouse 82. These modes include a command mode in which a health care professional at the remote monitor/controller 20 may transmit command signals to the infusion pump 12 to control its operation, a monitoring mode in which the infusion pump 12 will continually transmit the contents of its visual display 92 to the remote monitor/controller 20, a download data mode in which infusion data is transferred from the pump 12 to the remote monitor/controller 20, and a view data mode in which the infusion data may be viewed on the display 78 of the remote monitor/controller 20.

FIG. 10 illustrates a flowchart 450 of the basic operation of the remote monitor/controller 20. Referring to FIG. 10, at step 452, if the user selected the command mode described above, the routine branches to step 454 where a display of the keypad 90 of the infusion pump 12 is shown on the display device 78. The display shown at step 454 comprises a plurality of virtual entry keys having a spatial configuration substantially the same as the entry keys of the keypad 90 of the particular infusion pump type which is connected to the remote monitor/controller 20. An example of such a visual display is shown in FIG. 11A.

Figure 11A:
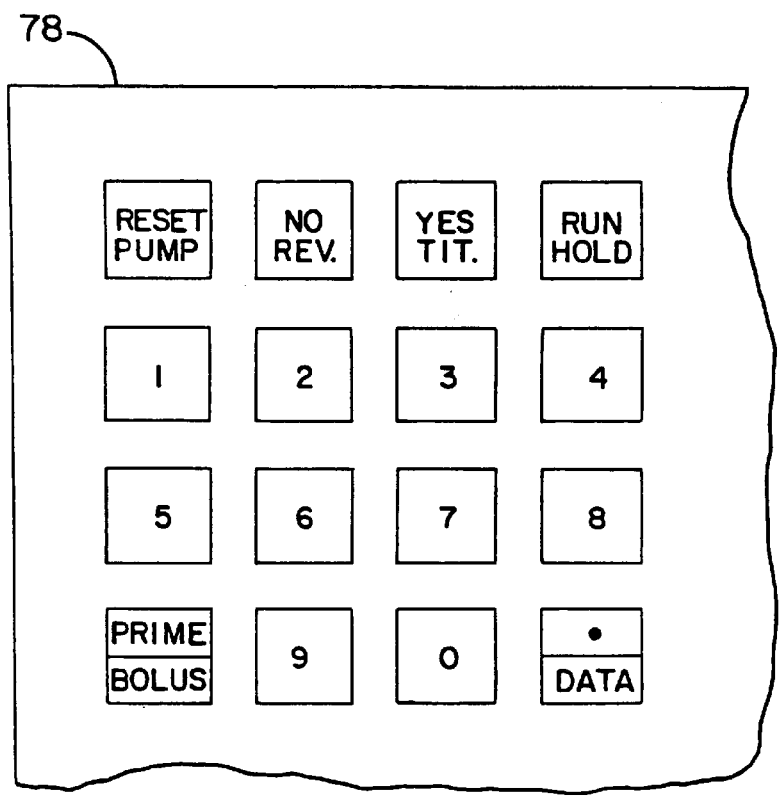
FIGS. 11A–11B illustrate portions of visual displays generated by the remote monitor/controller.
Figure 11B:
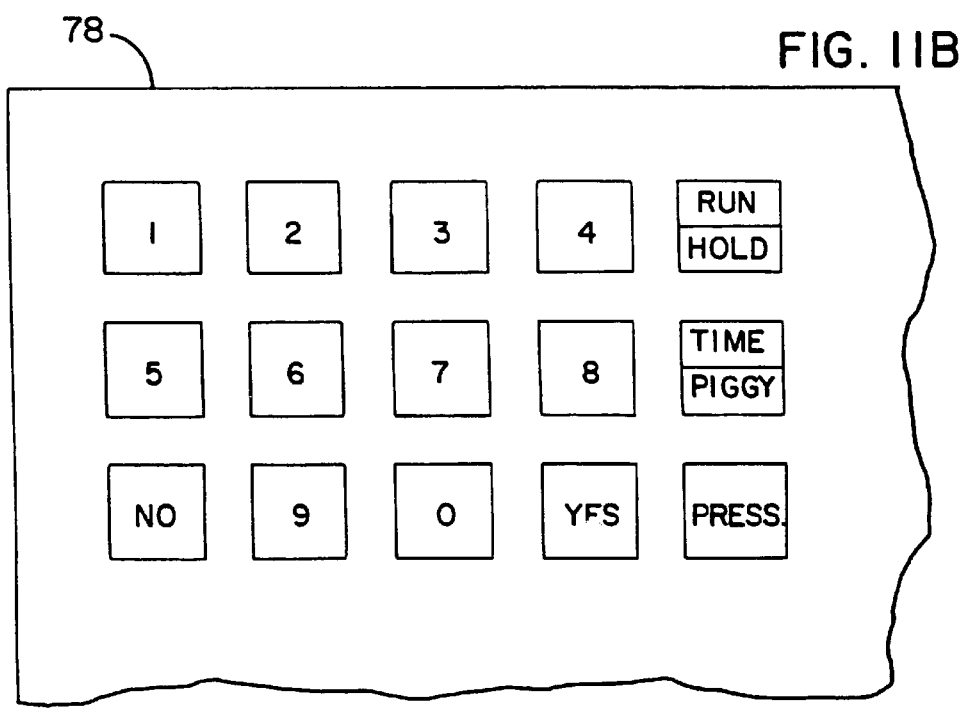

It should be noted that the virtual keypad shown in FIG. 11A is the same as the actual keypad 90 of the pump 12, which is shown in FIG. 3 (except that the on/off key of the pump 12 is replaced with a reset key in the virtual key display). Where a different type of pump having a different keypad is attached to the remote monitor/controller 20, that particular keypad is displayed on the display device 78. An example of a different virtual keypad is shown in FIG. 11B. Various virtual keypad configurations may be stored in the memory of the remote monitor/controller 20, each virtual keypad configuration having a pump type code associated therewith. Since the remote monitor/controller 20 initially determined the type of pump to which it was attached (via the routine of FIG. 9), it can retrieve from memory and display the corresponding virtual keypad for that type of pump.

After the virtual keypad is displayed, the health care professional may control the operation of the infusion pump 12 by selecting any of the virtual keys with the mouse 82. Other ways of selecting the keys could be utilized, such as a touch-sensitive screen or a display screen activated by radiation sensors. The infusion pump 12 responds to commands entered via its keypad 90 and to commands generated from the remote monitor/controller 20. At steps 456 and 458, any commands entered by the health care professional are transmitted to the infusion pump 12, and at steps 460 and 462, the display of the pump 12 is transferred to the remote monitor/controller 20 and displayed on the display device 78 of the remote monitor/controller 20. At step 464, if the user exits the command mode, the routine branches back to step 452.

At step 465, if the health care professional selected the monitor mode, the routine branches to step 466 where a visual display of the pump display 92 is shown on the display device 78. At step 467, the contents of the pump display 92 are transferred to the remote monitor/controller 20, and at step 468 those contents are displayed in the visual display generated at step 466. At step 469, if the user exits the monitor mode, the routine branches back to step 452; otherwise, the routine branches back to step 467 so that the contents of the pump display 92 are continuously shown on the display device 78 at step 468 (the display 92 of the infusion pump 12 changes in accordance with the pump operation so that the pump operation can be monitored by viewing the display 92). Step 467 may be accomplished, for example, by transmitting a pump display request to the pump 12 (via steps similar to steps 416–420 described above).

If the health care professional inputs a request to download data from the pump 12 to the remote monitor/controller 20 as determined at step 470, the routine branches to step 472 where the data transfer is accomplished, as described below in connection with FIGS. 13–14. If the user inputs a view data log request as determined at step 474, the routine branches to step 476 where data previously downloaded at step 472 can be viewed on the display device 78 of the remote monitor/controller 20. The user may exit the mode select routine 450 via step 478.

FIG. 12 illustrates one routine that could be used to implement the transmit command step 458 shown schematically in FIG. 10. Referring to FIG. 12, the pump command is transmitted from the remote monitor/controller 20 at step 480, and then the infusion pump 12 transmits to the remote monitor/controller 20 an echo of the command so that the remote monitor/controller 20 knows that command was received properly by the pump 21. The characters making up the echo are received at steps 482484, and if the echo is not correct, an error message is displayed to the health care professional. At step 490, the remote monitor/controller 20 sends an acknowledgement of the echo to the pump 12.

The transfer of data from the infusion pump 12 to the remote monitor/controller 20 shown schematically in step 468 of FIG. 10 is accomplished via a receive interrupt service routine 500 and a transmit interrupt service routine 550 that are performed by the infusion pump 12. Flowcharts of the routines 500, 550 are shown in FIGS. 13 and 14.

Figure 13:
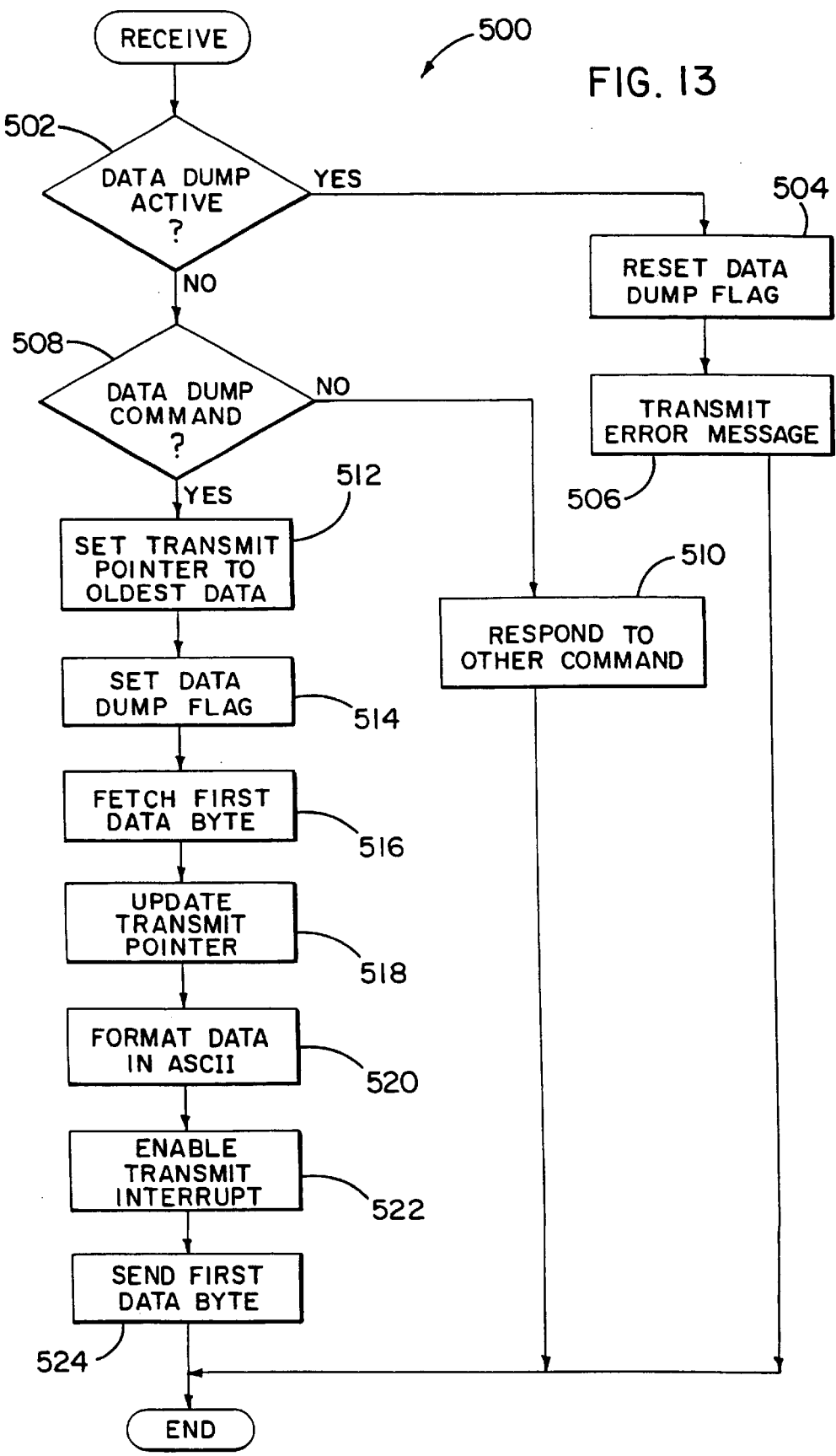
FIG. 13 is a flowchart of a receive routine that is performed by the infusion pump.
Figure 14:
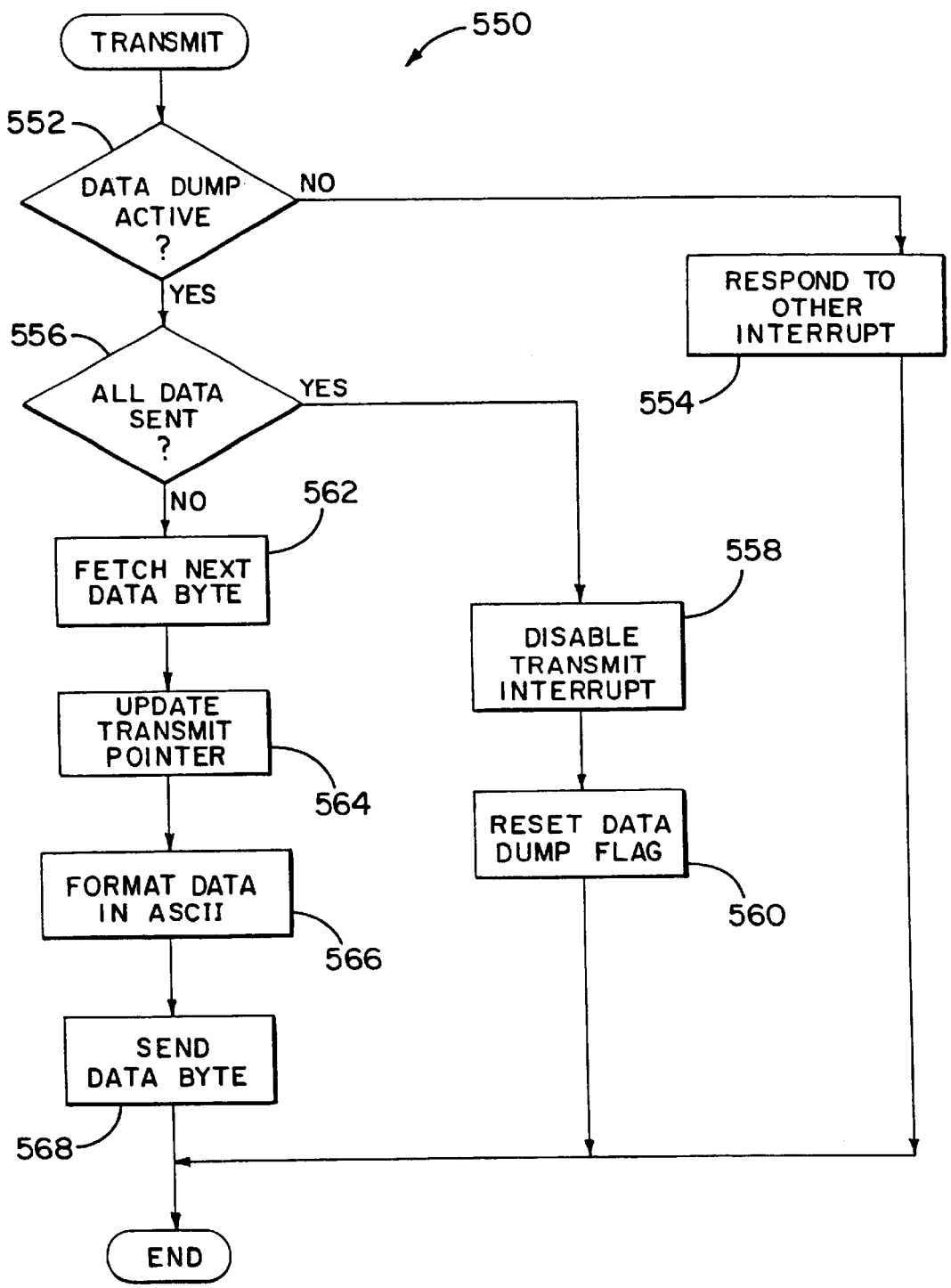
FIG. 14 is a flowchart of a transmit routine that is performed by the infusion pump.

The receive routine 500 shown in FIG. 13 is invoked upon the generation of a receive interrupt by the pump controller 100. The receive interrupt indicates that a message has been received in the receive buffer 118 of the controller 100 from the remote monitor/controller 20. When a download data command is sent to the infusion pump 12 (as determined at step 466 of FIG. 10), a data dump flag is set to logic "1," indicating that a data transfer or dump from the pump 12 to the remote monitor/controller 20 is in progress. The data transfer is performed in a segmented fashion. Instead of sending all of the infusion data and patient data stored in the RAM 104 to the remote monitor/controller 20 in a single, continuous stream, the data is sent in segmented portions, each of which is separated in time from its adjacent portions by a period of time, e.g. 100 microseconds.

Referring to FIG. 13, when the routine begins at step 502, a character or message will have been just received in the receive buffer 118. At step 502, if the data dump flag is active, meaning that a data transfer is already in progress, then the routine branches to step 504, where the data dump flag is set to logic "0," effectively terminating the data dump operation, and an error message is transmitted to the remote monitor/controller 20 at step 506. This is done to prevent the data dump operation from interfering with any commands that are transmitted from the remote monitor/controller 20 to the infusion pump 12.

If the data dump flag was not active as determined at step 502, the routine branches to step 508 where the message just received in the receive buffer 118 is checked to determine whether it is a data dump command. If it is not, then the routine branches to step 510 where the pump 12 responds to the command.

If the message is a data dump command, the routine branches to step 512 where a transmit pointer 513 (see FIG. 7) is set to the oldest data in the RAM 104 that has not yet been transmitted to the remote monitor/controller 20. At step 514, the data dump flag is set to logic "1" since a new data transfer operation is beginning. At step 516, the data byte specified by the transmit pointer 513 is retrieved from the RAM 104, and at step 518 the position of the transmit pointer 513 is updated (e.g. incremented) to point to the address of the next data byte to be transmitted. At step 520, the data byte retrieved at step 516 is formatted in ASCII; at step 522 the transmit interrupt is enabled; and at step 524 the reformatted data byte is transmitted from the infusion pump transmit buffer 116 to the remote monitor/controller 20 over the data link 38.

When the first data byte is sent out from the transmit buffer 116, a transmit interrupt is generated by the controller 100 to indicate that the transmit buffer 116 is empty and that another data byte can be transmitted. Upon the generation of the transmit interrupt, the transmit routine 550 is performed. Referring to FIG. 14, at step 552 the status of the data dump flag is checked. If the flag is not active, meaning that a data dump operation is not in progress, the routine branches to step 554 where the routine responds to the other interrupt. If the data dump flag is active, then the routine branches to step 556, where it determines whether all of the segmented portions of the infusion data have been transmitted. This may be accomplished, for example, by determining if the transmit pointer 513 and the pointer 376 (FIG. 7) are pointing to the same memory location. If all the requested data has been sent, the routine branches to step 558, where the transmit interrupt is disabled, and then to step 560 where the data dump flag is reset to logic "0," effectively ending the data transfer operation.

If not all the data has been transferred as determined at step 556, the routine branches to step 562 where the data byte specified by the transmit pointer 513 is retrieved from the RAM 104. At step 564 the position of the transmit pointer is updated to point to the address of the next data byte to be transmitted. At step 566, the data byte retrieved at step 562 is formatted in ASCII, and at step 568 the reformatted data byte is transmitted from the infusion pump transmit buffer 116 to the remote monitor/controller 20 over the data link 38.

The transmit interrupts generated by the controller 100 to transfer the segmented data portions to the remote monitor/controller 20 are assigned a lower priority than the interrupts generated in response to input of the shaft encoder sensor 130, which is necessary to provide the desired infusion rate. Consequently, the transfer of the infusion data and patient data does not interfere with the ability of the pump 12 to provide the desired infusion rate, and the data transfer can occur while the pump is infusing the patient with the medicant.

FIG. 15 is an illustration of a graphical user menu that may be shown on the display device 78 of the remote monitor/controller 20. The health care professional may select particular data for transfer or viewing, via a number of different parameters such as beginning date, ending date, types of data, etc. The particular manner in which particular data may be selected for transfer or viewing is not considered important to the invention.

Figure 16:
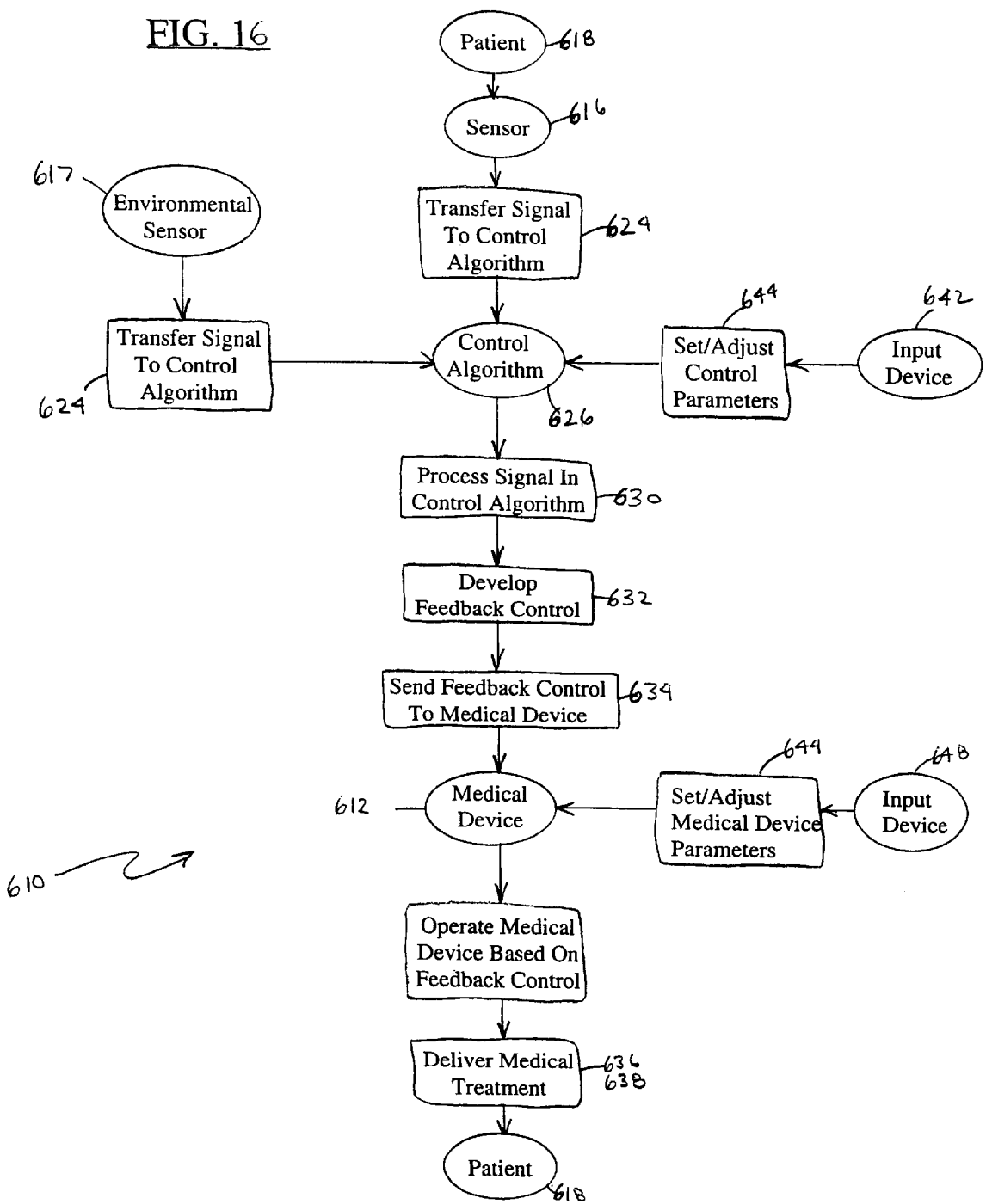
FIG. 16 is a block diagram of a medical treatment administration system of the present invention.

Additionally, FIGS. 16–24 show a medical treatment administration system 610 utilizing a medical treatment delivery control to distribute the medical treatment based on the condition of the specific patient and/or a change in the environment of the specific patient. As shown in FIG. 16, one embodiment of the medical treatment administration system 610 includes a medical device 612, which may be an infusion pump 12, a control algorithm 626 coupled to the medical device 612, and a sensor 616 coupled to the patient 618. The medical device 612 may be one of a variety of devices, including, but not limited to infusion pumps, ventilators, insulin delivery devices, and anesthesia delivery devices, however, one of ordinary skill in the art would understand that other medical devices could be utilized without departing from the scope of the invention. Additionally, the medical device 612 may be programmable as disclosed above, and further as understood by one of ordinary skill in the art.

In one embodiment, the infusion pump 12, illustrated in FIG. 3, is utilized as the medical device 612 for administering a liquid medicant to the patient 618. Typically, the medical device 612 has a supply of medication (not shown) and a means for delivering the medication (not shown) to the patient 618. With the infusion pump 12, the supply of medication is typically a liquid medicant retained in a syringe or IV-type bag. Additionally, with an infusion pump 12 the means for delivering the medication includes a liquid injection device, often a hollow needle or catheter, adapted to be connected to the patient, a conduit or tubing connected to the liquid injection device, a pumping mechanism for pumping the liquid medicant through the conduit and into the patient via the liquid injection device, and a controller for controlling the pumping mechanism. However, when other types of medical devices are utilized, the medical treatment and the means for delivering the treatment will likely vary to be in accord with the specific medical device. For example, a ventilator provides oxygen to the patient, an insulin delivery mechanism delivers insulin to the patient, and an anesthesia device provides anesthesia gas or anesthesia medication to the patient, each with the appropriate delivery means.

In the embodiment illustrated in FIG. 16, the sensor 616 is coupled to the patient 618 and receives information from the patient 18 concerning the physiological condition of the patient 618. As is understood by one of ordinary skill in the art, such physiological conditions may include, but are not limited to, the patient's heart rate, the patient's body temperature, the patient's blood pressure, the patient's activity level, the patient's cellular metabolism, the patient's cellular proliferation, the patient's metabolic demand, the patient's food intake, and the patient's SpO$_2$ level, etc. Such factors, as well as other factors known by one of ordinary skill in the art, are understood to be triggering events for the distribution of medical treatment, and especially drug therapy, to individuals in the treatment of medical conditions. Additionally, the sensing device may comprise an input device for receiving a manual input. The manual input may be provided by a health care provider or the patient. One example of the patient providing input for the sensing device is where the medical device 612 is a insulin delivery mechanism. As such, the patient may provide input to the sensor indicating the type of food consumed by the patient.

In one embodiment, multiple sensors 616 are comprised in a portable multiparametric physiological monitor (not shown) for continuous monitoring of certain physical parameters of the patient. The monitor has sensors 616, including: EKG electrodes, a chest expansion sensor, an accelerometer, a chest microphone, a barometric pressure sensor, a body temperature sensor and an ambient temperature sensor. Each of the sensors provides an output signal to an analog-to-digital converter (ADC).

In such an embodiment, the sensors 616 may be provided in a body strap (not shown) which, could comprise a chest strap upon which are distributed the various sensors and supporting electronics. (It will be recognized by those skilled in the art that a multiparametric monitoring device may also be mounted by a strap about a part of the body other than the chest). The chest strap is adapted to fit around the torso of the patient 618.

The variety of parametric sensors 616 are located on the strap as most appropriate for the parameter (or parameters) which it detects. Each of the sensors 616 provides an electrical input to analog circuitry which filters and amplifies the sensor signals, as known in the art of signal processing, and outputs them to an analog-to-digital converter, which may be part of controller hardware. The sensors in the strap may be as follows: a pectoralis temperature sensor which senses the temperature of the surface of the patient's chest; barometric pressure sensor which senses the ambient barometric pressure of the patient's environment; chest expansion (ventilation) sensor which detects the tension on the chest strap as an indication of the expansion and contraction of the patient's chest; accelerometer which detects movement and inclination of the patient's body; ambient temperature sensor which senses the ambient temperature of the patient's environment; microphone which detects sounds from within the patient's torso; underarm temperature sensor which senses the temperature of the side of the patient's torso underneath the arm; and, EKG electrodes which detect electrical signals caused by action of the heart muscle. The EKG electrodes are used in combination with ground, or reference, electrodes, and are placed in contact with the skin of the patient's chest to detect electrical signals generated by the pumping action of the patient's heart muscle. The EKG (electrocardiogram) is an indication of the patient's heart activity, as is well known in the a field of medicine.

Also as shown in FIG. 16, sensor 617 may be provided in addition to, or in substitution of, sensor 616. Sensor 617 obtains information concerning the environment of the patient 618. Typically, the sensors 616, 617 automatically obtain the signal concerning the physiological condition of the patient and/or the condition of the environment, respectively, without intervention from the patient 618. Depending on the information required by the control algorithm 626, multiple sensors 616, 617 may be utilized in series or in parallel (FIGS. 16, 19, 22 and 23).

Figure 19:
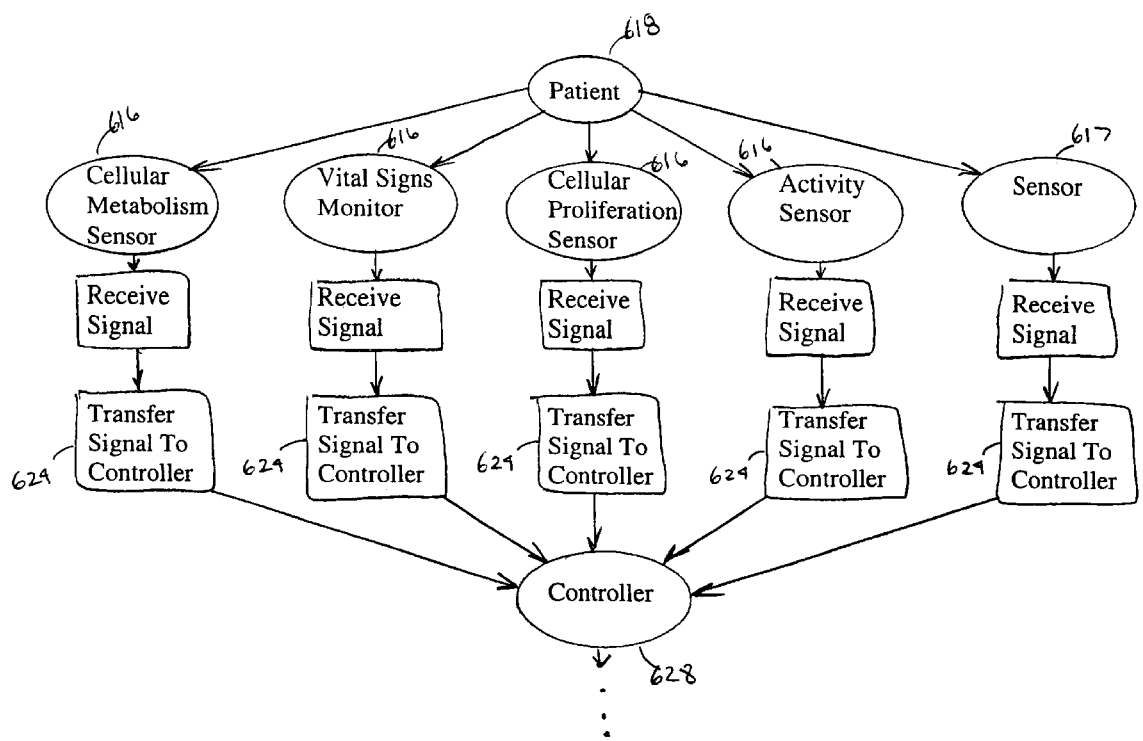
FIG. 19 is a block diagram of another variation of the medical treatment administration system of FIG. 16, including a variety of sensing devices.
Figure 20:
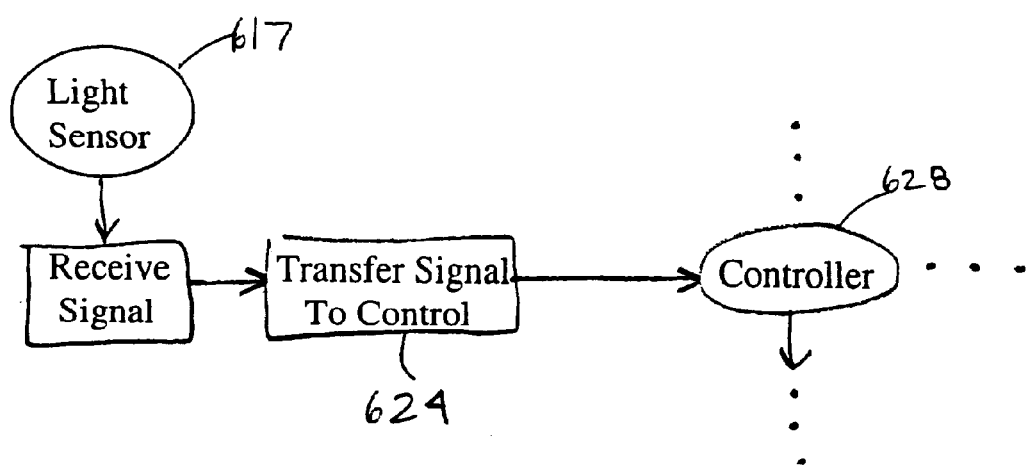
FIG. 20 is a block diagram of another variation of the medical treatment administration system of FIG. 16, including a variety of sensing devices.

The sensors 616, 617 may be any device that is capable of receiving a signal (i.e., information), whether from an individual 616, such as a signal concerning the individuals heart rate, body temperature, blood pressure, activity level, cellular metabolism, cellular proliferation, metabolic demand, $SpO_2$ level, etc., or based on an environmental condition 617, such as the ambient temperature, ambient light condition, etc. As shown in FIGS. 19 and 20, such sensors 616, 617 may include, but are not limited to, vital signs monitors, blood pressure monitors, light sensors, environmental sensors and activity sensors. Additionally, as shown in FIG. 62, rather than being a separate component, the sensors 616, 617 may be integral with the controller 628.

Figure 17:
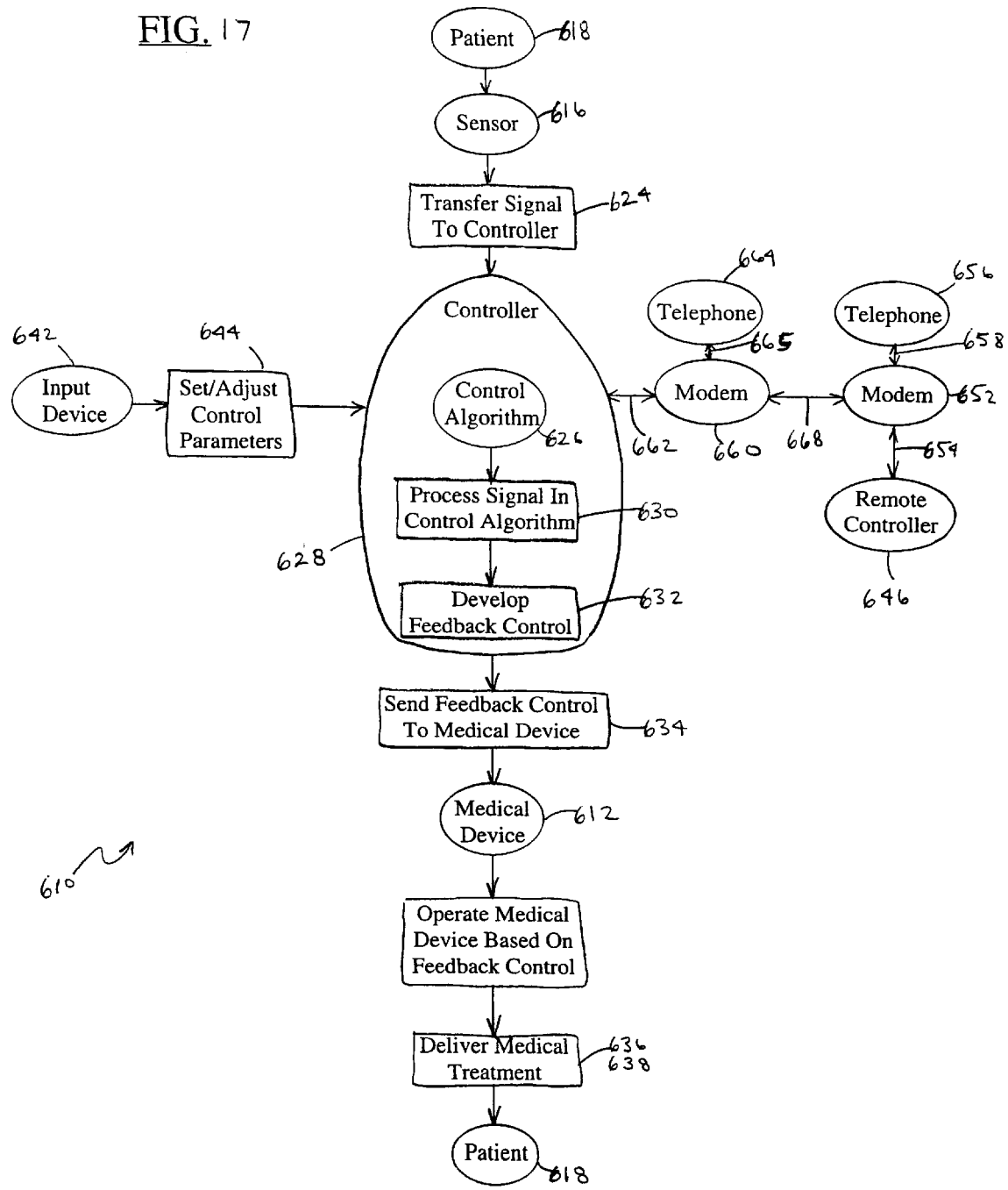
FIG. 17 is a block diagram of a variation of the medical treatment administration system of FIG. 16, including remote controlling.
Figure 18:
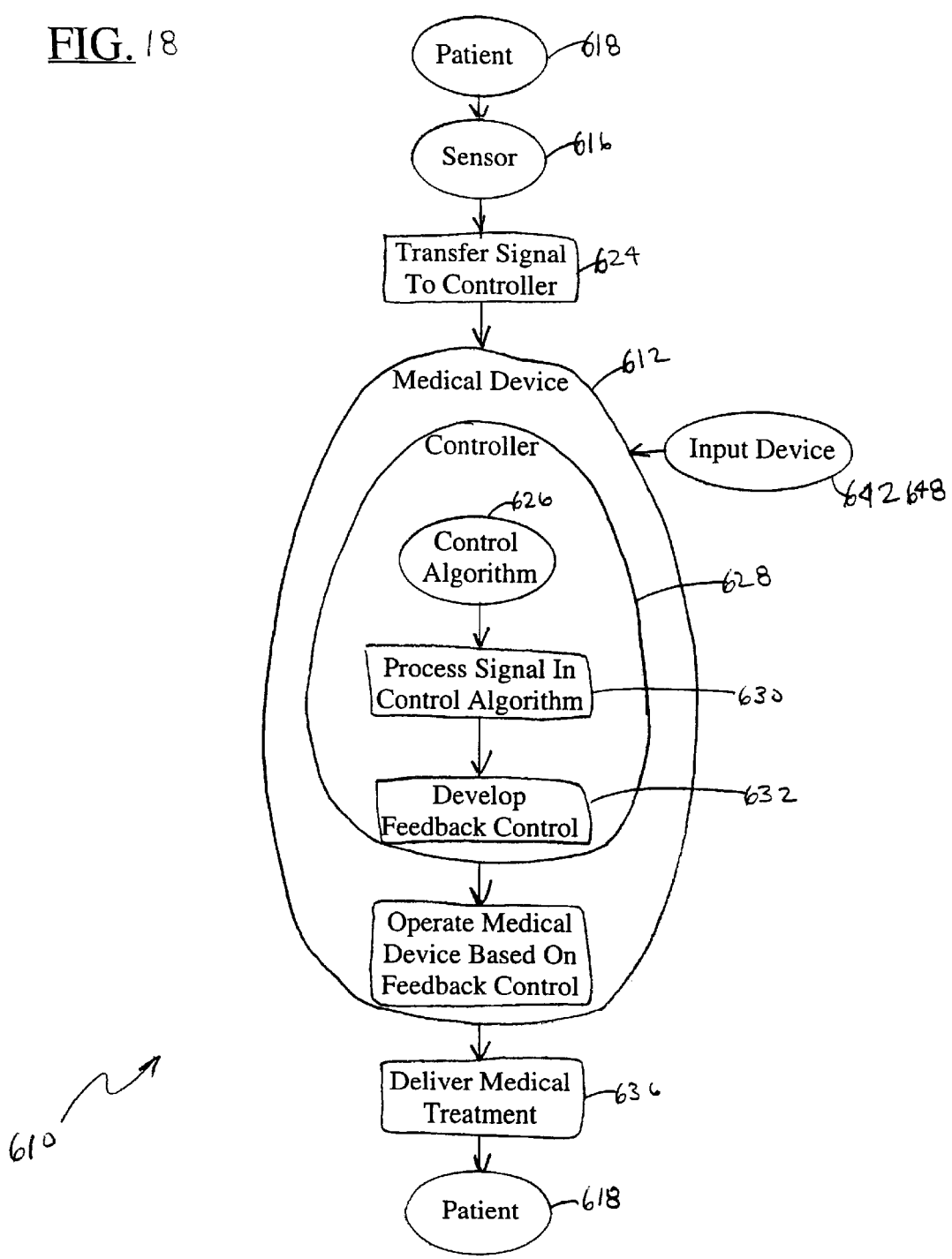
FIG. 18 is a block diagram of another variation of the medical treatment administration system of FIG. 16, including where the controller is a component of the medical device.
Figure 21:
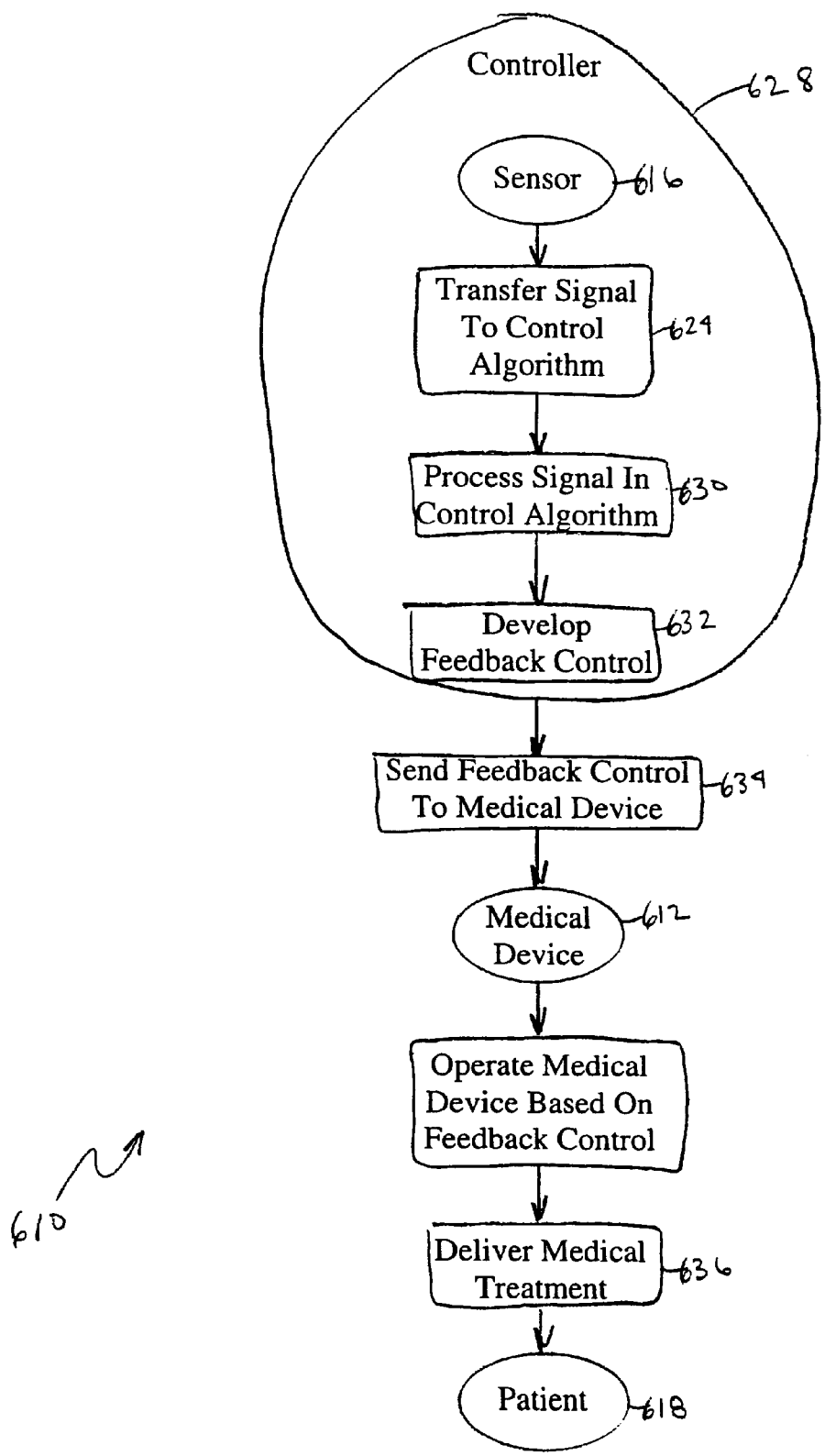
FIG. 21 is a block diagram of another variation of the medical treatment administration system of FIG. 16, including where the controller and the sensing device are an integral component.

The signal received from the sensor 616, 617 is electrically transferred 624 to a control algorithm 626. As shown in FIGS. 17, 18 and 21, the control algorithm 626 may be a part of the controller 628 (also referred to as a processor). Additionally, as shown in FIG. 18, the controller 628 may be a component of the medical device 612. Depending on the specific medical treatment to be administered to the patient 618, the control algorithm 626 may request signals from one or more sensors 616, 617. While it is understood that the rest-activity or metabolism cycle of a patient can be determined invasively by measuring various elements including blood cell counts, plasma or serum concentration of cortisol, liver enzymes, and creatine, other methods may also be available. For example, the rest-activity or metabolism cycle of a patient can also be measured non-invasively by the vital sign or activity of the patient. Additionally, it has been found that the body temperature of a patient drops during the night, and that a patient's heart rate drops when the patient is at rest. Accordingly, such signals are obtained by the sensors 616, 617, and such information is transferred 624 to the control algorithm 626 for processing.

Figure 24:
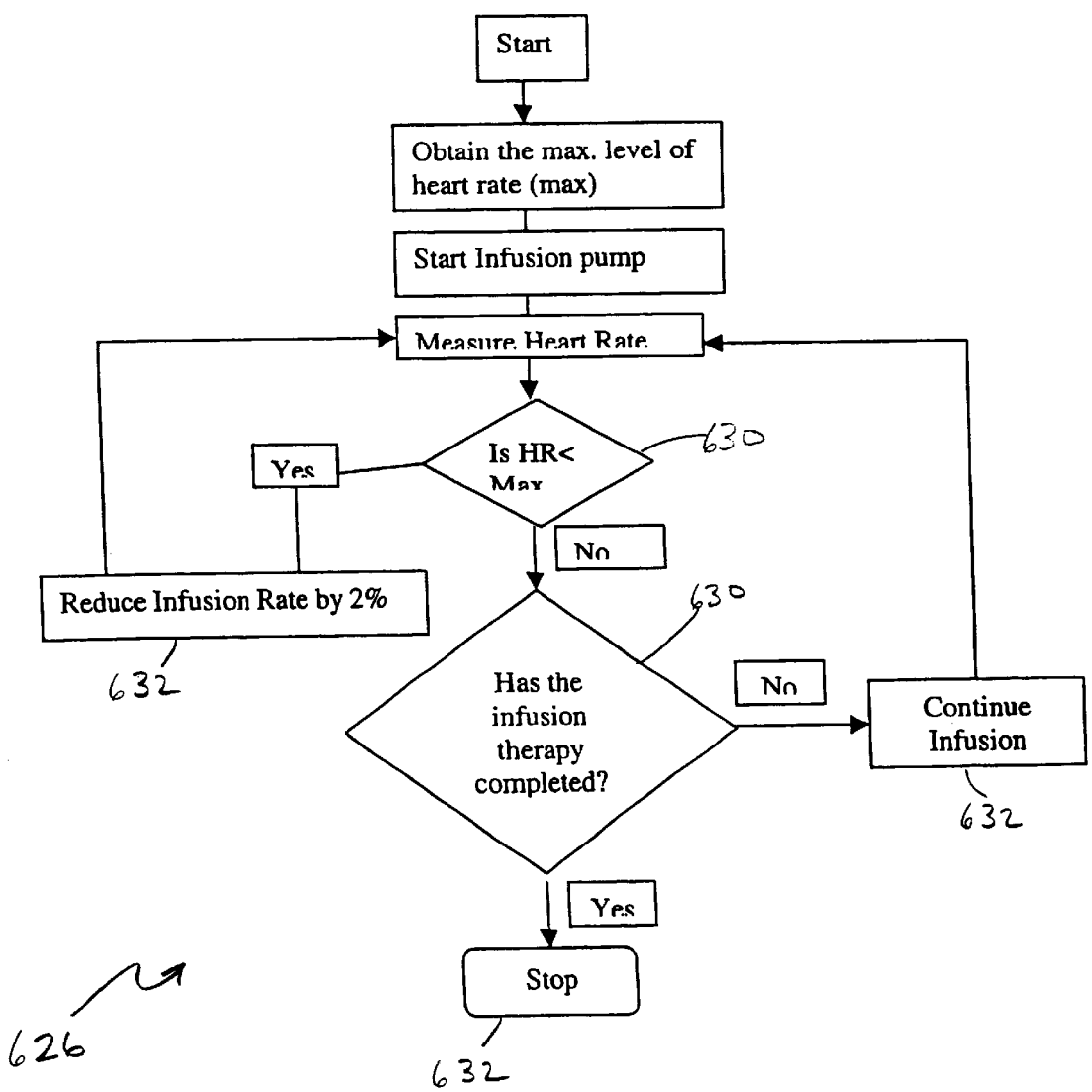

It is understood that the control algorithm 626 will likely be different for each different medical treatment, and further it is also understood that the control algorithm 626 may be different for different patients, even for the same medical treatment. One example of a control algorithm 626 is shown in FIG. 24. As shown in FIG. 24, the control algorithm 626 is utilized to control the delivery of medication to a patient as a function of the patient's 618 heart rate. In this embodiment, the control algorithm 626 receives a signal of the patient's heart rate from one of the sensors 616. The control algorithm 626 processes the signal 630 by comparing the signal with the maximum heart rate. If the heart rate signal is less than the maximum heart rate signal the control algorithm develops a feed back control 632 to reduce the rate of infusion of the infusion pump 12 by 2%. If the heart rate signal is not less than the maximum heart rate signal the control algorithm further determines if the infusion therapy has been completed. If the infusion therapy has not been completed, feedback control 632 is provided to continue infusion. Additional processing 630 of the heart rate signal is subsequently continued. If the infusion therapy has been completed, feedback control 632 is provided to stop the infusion pump 12.

After the control algorithm 626 receives the transferred signal 624 it processes 630 the signal through the control algorithm 626 and the resultant feedback control 632 is developed. If multiple signals are requested and received from a plurality of sensors 616, 617, each required signal is processed 630 through the control algorithm 626 as programmed, and a resultant feedback control 632 is developed. The feedback control 632 operates as a control signal for the medical device 610 to control or regulate delivery of the medical treatment to the patient 618.

This is accomplished by transferring 634 the feedback control 632 that was developed by the control algorithm 626 to the medical device 610. The feedback control 632 provides the commands for operation of the medical device 610. The feedback control 632 typically provides one of two signals or commands to the medical device 610: deliver 636 medical treatment to the patient 618 or do not deliver 638 medical treatment to the patient. If the feedback control 632 provides a signal to deliver 636 the medical treatment it may also provide a signal to the medical device 612 indicating the amount and rate of treatment to provide to the patient 618. Such a signal may include increasing or decreasing the rate of medication delivery.

Figure 22:
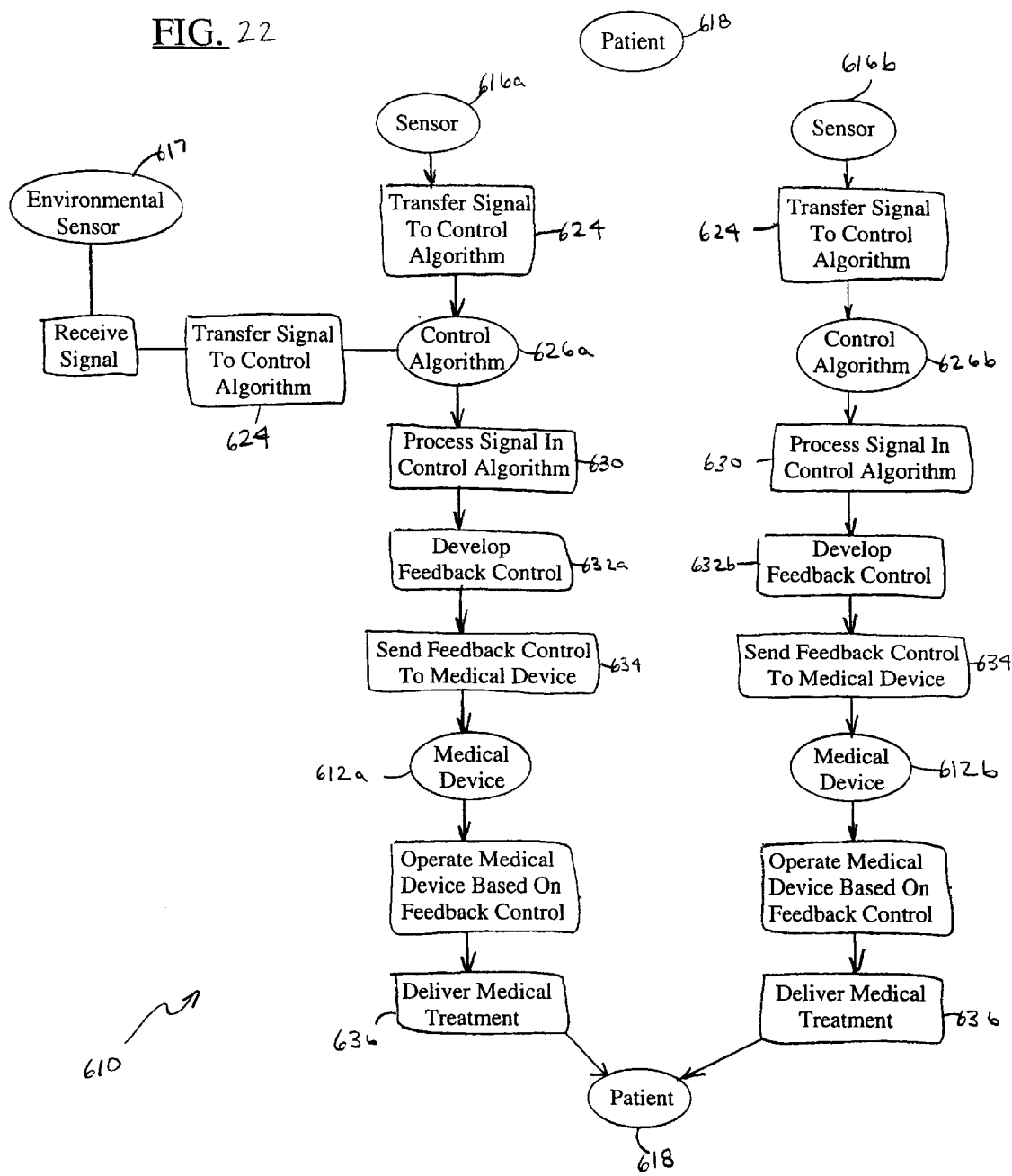
FIG. 22 is a block diagram of another variation of the medical treatment administration system of FIG. 16, including a plurality of medical treatment devices.

As shown in FIG. 22, multiple medical devices 612a, 612b may be utilized to deliver 636 medical treatments to the patient 618. The specific medical treatments may be the same, and may merely be dosed differently, or each medical device 612a, 612b may deliver 636 a different medical treatment to the patient 618. Further, as also shown in FIG. 22, separate control algorithms 626a, 626b may be utilized for each medical device 612a, 612b, respectively. The embodiment of FIG. 22, utilizes two distinct control algorithms 626a, 626b, and numerous sensors 616a, 616b and 617. Sensors 616a, 617 transfer 624 signals to control algorithm 626a, which, depending on the treatment to be delivered 636 to the patient 618, may process 630 the signals from one or both of the sensors 616a, 617 to develop a resultant feedback control 632a. Sensor 616b transfers 624 a signal to control algorithm 626b which likewise processes 630 the signal and develops a resultant feedback control 632b. Feedback control 632a is sent to the first medical device 612a to control the delivery 636a of medical treatment to the patient 618, while feedback control 632b is sent to the second medical device 612b to control the delivery 636b of medical treatment to the same patient 618.

Figure 23:
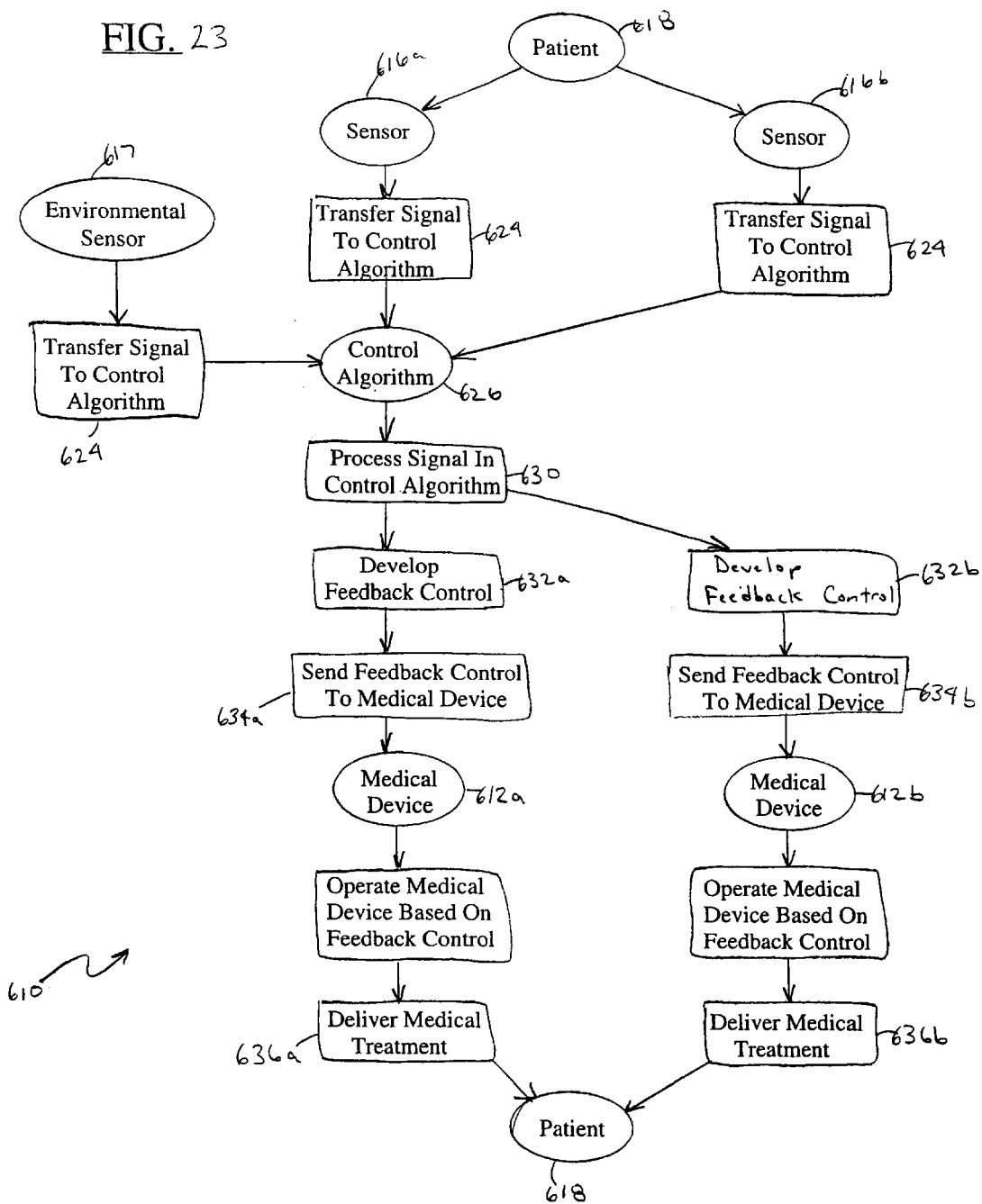
FIG. 23 is a block diagram of another variation of the medical treatment administration system of FIG. 22, including a processor for a plurality of medical treatment devices; and, FIG. 24 is a block diagram of one type of a control algorithm of the present invention.

Conversely, as shown in FIG. 23, one control algorithm 626 may control multiple medical devices 612a, 612b. In this embodiment, one control algorithm 626 is utilized with a plurality of sensors 616a, 616b and 617. Sensors 616a, 616b and 617 transfer 624 signals to the control algorithm 626, which, depending on the treatment to be delivered 636 to the patient 618, may process 630 the signals from one or more of the sensors 616a, 616b and 617 to develop one or more resultant feedback controls 632a, 632b. Feedback control 632a is sent to the first medical device 612a to control the delivery 636a of medical treatment to the patient 618, while feedback control 632b is sent to the second medical device 612b to control the delivery 636b of medical treatment to the same patient 618. Accordingly, in this embodiment the control algorithm 626 for the first medical device 612a is the same control algorithm 626 as for the second medical device 612b.

Because the medical treatment apparatus 610 may be utilized with different treatment therapies, the control algorithm 626 is generally modified or changed for each different treatment therapy. Thus, as shown in FIGS. 16 and 17, an input device 642 is generally provided to adjust and set the control parameters 644 of the control algorithm 626. The input device 642 may be coupled to the controller 628 or directly to the control algorithm 626. While the control algorithm 626 may be manually input, it may also be dynamically downloaded as from a database or network.

Further, as shown in FIG. 16, the medical device 612 may also have an input device 648 therefor. The input device 648 for the medical device 612 allows a user, typically an authorized clinician to enter control commands 650 to adjust or set control parameters for the medical device 612. In an alternate embodiment, the input device for the medical device 612 is the same as the input device for the controller/control algorithm.

As shown in FIG. 17, a remote controller 646 (i.e., a remote input device) may be provided for remotely adjusting or setting the control parameters of the control algorithm 26 and/or controller 28. U.S. Pat. No. 5,885,245, assigned to the assignee of the present invention, discloses a remote controller, among other things, and is expressly incorporated herein by reference, and made a part hereof. The remote controller 646 is disposed at a room location (i.e. a second location) remote from the room location at which the medical device 612 is located (i.e., a first location). The remote controller 646 could be disposed in a different room of the same building in which the medical device 612 is disposed, or in a different building than the one in which the medical device 612 is disposed. The remote controller 646 is connected to a conventional voice/data modem 652 via a data link 654, and the modem 652 is also connected to a telephone 656 via a voice link 658. The medical device 612 is connected to a conventional voice/data modem 660 via a data link 662, and the modem 660 is connected to a telephone 664 via a voice link 665. The two modems 652, 660 are interconnected to bidirectional voice and data communication via a communication link 668, which could be a telephone line, for example. Additionally, the remote controller 646 may communicate with the control algorithm 626 via an internet, an intranet and a wireless network. Furthermore, the remote controller 626 may be a server.

While the specific embodiments have been illustrated and described, numerous modifications come to mind without significantly departing from the spirit of the invention, and the scope of protection is only limited by the scope of the accompanying claims.

What is claimed is:

1. A remotely-controlled medication delivery system, comprising:
    a medical treatment device having a supply of medication and a means for delivering the medication to the patient, the medical treatment device being disposed in a first location;
    a control algorithm coupled to the medical device;
    a sensing device coupled to the control algorithm, the sensing device sending a signal to the control algorithm, wherein the control algorithm processes the signal received from the sensing device and develops a feedback control based on a result of processing the signal to determine whether medication should be delivered from the medical treatment device to the patient, and providing the feedback control to the medical treatment device to control the delivery of the medical treatment to the patient; and,
    a remote controller disposed at a second location remote from the first location, the remote controller having an input device to control operation of the control algorithm.

2. The remotely-controlled medication delivery system of claim 1, wherein the remote controller communicates with the control algorithm via an internet.

3. The remotely-controlled medication delivery system of claim 1, wherein the remote controller communicates with the control algorithm via an intranet.

4. The remotely-controlled medication delivery system of claim 1, wherein the remote controller communicates with the control algorithm via a wireless network.

5. The remotely-controlled medication delivery system of claim 1, wherein the remote controller is a server.

6. The remotely-controlled medication delivery system of claim 1, wherein the medical treatment device comprises an infusion pump for administering a liquid medicant to the patient, the infusion pump having liquid injection device adapted to be connected to the patient, a conduit connected to the liquid injection device, a pumping mechanism for pumping the liquid medicant through the conduit and into the patient via the liquid injection device, and a pump controller for controlling the pumping mechanism, the pump controller receiving the feedback control to the medical treatment device to control the delivery of the medical treatment to the patient.

7. The remotely-controlled medication delivery system of claim 1, wherein the sensing device comprises a sensor coupled to the patient to receive information from the patient concerning the physiological condition of the patient, the information being converted into a signal.

8. The remotely-controlled medication delivery system of claim 7, wherein the sensor is a vital signs monitor.

9. The remotely-controlled medication delivery system of claim 1, wherein the sensing device comprises a sensor that receives information concerning the patient's environment.

10. The remotely-controlled medication delivery system of claim 9, wherein the sensor is a light sensor.

11. The remotely-controlled medication delivery system of claim 1, further comprising:
a local input device coupled to the control algorithm, the local input device being located in the first location.

12. The remotely-controlled medication delivery system of claim 11, wherein the local input device has a plurality of entry keys disposed in a spatial configuration, and wherein the remote controller has a display, the medication delivery system further comprising a means operatively coupled to the display for generating a visual display of a plurality of virtual entry keys having a spatial configuration substantially the same as the entry keys of the local input device.

13. A remotely-controlled medication delivery system for delivering a medical treatment to a patient from a medical device capable of delivering the medical treatment, comprising:
a sensor receiving a signal, a control algorithm operatively connected to the sensor, and a remote input device disposed at a location remote from the sensor, wherein the sensor obtains the signal, the control algorithm processing the signal obtained by the sensor and develops a feedback control adapted to control the delivery of the medical treatment from the medical device to the patient, and wherein the remote input device has a means for manipulating operation of the control algorithm.

14. The medication delivery system of claim 13, further comprising a medical device having a supply of medical treatment and a means for delivering the medical treatment to the patient, the medical device operatively coupled to the control algorithm, the control algorithm controlling the delivery of the medical treatment from the medical device to the patient.

15. The medication delivery system of claim 13, further comprising a local input device operatively connected to the control algorithm, the local input device controlling the process parameters of the control algorithm.

16. The medication delivery system of claim 13, further comprising a display connected to the remote input device, the display providing a visual readout of the control algorithm.

17. The medication delivery system of claim 13, wherein the sensor is operatively coupled to the patient and receives information concerning the physiological condition of the patient.

18. A medication delivery system, comprising:
a programmable medical device located at a first location for administering a medical treatment to a patient, wherein the programmable medical device has a means for administering the medical treatment to the patient, and wherein the programmable medical device has a first input device for entering control commands for the programmable medical device;
a local controller operatively connected to the programmable medical device, the local controller being disposed at the first location and having a second input device for entering control commands for the local controller, the local controller also being operatively connected to the patient to receive a signal from the patient, wherein the local controller manipulates operation of the programmable medical device; and,
a remote controller for controlling the local controller, the remote controller being disposed at a second location remote from the first location at which the programmable medical device is disposed, said remote controller having means to allow a user at the second location to control the local controller.

19. The medication delivery system of claim 18, wherein the second input device is a bar code reader.

20. The medication delivery system of claim 18, wherein patient information and medical data is entered via the second input device.

21. The medical apparatus of claim 18, further comprising:
a display device, display means for generating a visual display of a virtual input device substantially corresponding to said input device of said programmable medical device, the display means operatively coupled to the display device, and means for allowing a user at the second location to activate the virtual input device to allow the user to control the operation of the programmable medical device from the second location.

22. A method to provide medication to a patient where the medication delivery is triggered by one or more physiological conditions of the patient, comprising the steps of:
providing a medication delivery device;
providing a local controller having a control algorithm;
providing a sensor;
providing a remote controller, the remote controller having an input device; and,
utilizing the sensor to obtain a signal concerning the physiological condition of the patient, transferring the signal to the controller, entering information contained in the signal in the control algorithm, developing a result based on resulting data from the control algorithm, developing feedback control based on the result from the control algorithm, and manipulating the medication delivery device as appropriate based on the feedback control to deliver the medication to the patient.

23. A method to provide medication to a patient where the medication delivery is triggered by one or more environmental conditions, comprising the steps of:
providing a medication delivery device;
providing a local controller having a control algorithm;
providing a sensor;
providing a remote controller, the remote controller having an input device; and,
utilizing the sensor to obtain a signal concerning an environmental condition of the patient's environment, transferring the signal to the controller, entering information contained in the signal in the control algorithm, developing a result based on resulting data from the control algorithm, developing feedback control based on the result from the control algorithm, and manipulating the medication delivery device as appropriate based on the feedback control to deliver the medication to the patient.

* * * * *